United States Patent
Bourin et al.

(10) Patent No.: US 9,394,286 B2
(45) Date of Patent: Jul. 19, 2016

(54) ROCK INHIBITORS

(71) Applicant: Amakem NV, Diepenbeek (BE)

(72) Inventors: Arnaud Pierre Jean Bourin, Diepenbeek (BE); Dirk Leysen, Diepenbeek (BE); Olivier Defert, Diepenbeek (BE); Sandro Boland, Diepenbeek (BE)

(73) Assignee: Amakem NV, Diepenbeek (BE)

( * ) Notice: Subject to any disclaimer, the term of this patent is extended or adjusted under 35 U.S.C. 154(b) by 0 days.

(21) Appl. No.: 14/437,919

(22) PCT Filed: Oct. 31, 2013

(86) PCT No.: PCT/EP2013/072774
§ 371 (c)(1),
(2) Date: Apr. 23, 2015

(87) PCT Pub. No.: WO2014/068035
PCT Pub. Date: May 8, 2014

(65) Prior Publication Data
US 2015/0299173 A1   Oct. 22, 2015

(30) Foreign Application Priority Data
Oct. 31, 2012   (EP) .................................... 12190859

(51) Int. Cl.
| C07D 401/12 | (2006.01) |
| --- | --- |
| C07D 405/14 | (2006.01) |
| A61K 31/4725 | (2006.01) |
| A61K 31/454 | (2006.01) |
| C07D 217/04 | (2006.01) |
| C07D 405/12 | (2006.01) |

(52) U.S. Cl.
CPC ............ *C07D 405/14* (2013.01); *C07D 217/04* (2013.01); *C07D 401/12* (2013.01); *C07D 405/12* (2013.01)

(58) Field of Classification Search
None
See application file for complete search history.

(56) References Cited

U.S. PATENT DOCUMENTS

| 2009/0325959 A1 | 12/2009 | Vittitow et al. |
| --- | --- | --- |
| 2009/0325960 A1 | 12/2009 | Fulcher et al. |

FOREIGN PATENT DOCUMENTS

| EP | 1256574 A1 | 11/2002 |
| --- | --- | --- |
| WO | 0156988 A1 | 8/2001 |
| WO | 2008077057 A2 | 6/2008 |
| WO | 2009158587 A1 | 12/2009 |
| WO | 2010065782 A1 | 6/2010 |
| WO | 2011075415 A1 | 6/2011 |
| WO | 2012015760 A1 | 2/2012 |

OTHER PUBLICATIONS

International Search Report and Written Opinion completed Nov. 25, 2013 pertaining to PCT/EP2013/072774 filed Oct. 31, 2013.
European Search Report completed Apr. 4, 2013 pertaining to EP12190859.4 filed Oct. 31, 2012.
Iwakubo et al., "Design and synthesis of Rho kinase inhibitors (II)", Bioorganic & Medicinal Chemistry 15 (2007) pp. 350-364; www.sciencedirect.com.
Iwakubo et al., "Design and synthesis of Rho kinase inhibitors (III)", Bioorganic & Medicinal Chemistry 15 (2007) pp. 1022-1033; www.sciencedirect.com.
Schröter et al., "Detection of myosin light chain phosphorylation—A cell-based assay for screening Rho-kinas inhibitors", Biochemical and Biophysical Research Communications 374 (2008) pp. 356-360.

*Primary Examiner* — Zinna Northington Davis
(74) *Attorney, Agent, or Firm* — Dinsmore & Shohl LLP

(57) ABSTRACT

The present invention relates to new kinase inhibitors, more specifically ROCK inhibitors, compositions, in particular pharmaceuticals, comprising such inhibitors, and to uses of such inhibitors in the treatment and prophylaxis of disease. In particular, the present invention relates to new ROCK inhibitors, compositions, in particular pharmaceuticals, comprising such inhibitors, and to uses of such inhibitors in the treatment and prophylaxis of disease. In addition, the invention relates to methods of treatment and use of said compounds in the manufacture of a medicament for the application to a number of therapeutic indications including sexual dysfunction, inflammatory diseases, ophthalmic diseases and Respiratory diseases. Compounds of the invention display soft drug characteristics, i.e. they are rapidly inactivated upon entry in the systemic circulation. Therefore, they allow for reduced systemic exposure to functionally active ROCK inhibitors.

(I)

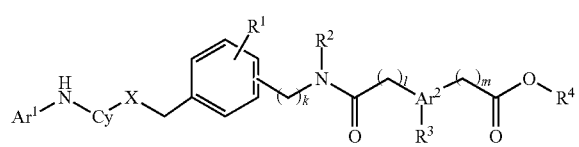

16 Claims, 1 Drawing Sheet

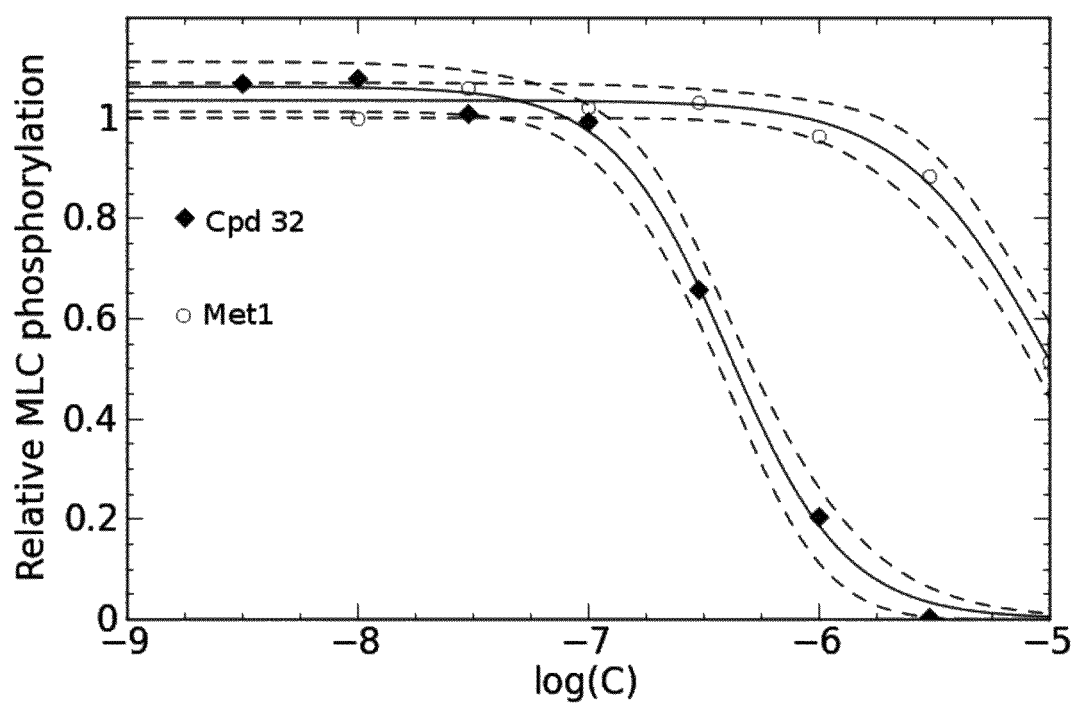

ROCK INHIBITORS

FIELD OF THE INVENTION

The present invention relates to new kinase inhibitors, more specifically ROCK inhibitors, compositions, in particular pharmaceuticals, comprising such inhibitors, and to uses of such inhibitors in the treatment and prophylaxis of disease. In particular, the present invention relates to new ROCK inhibitors, compositions, in particular pharmaceuticals, comprising such inhibitors, and to uses of such inhibitors in the treatment and prophylaxis of disease. Compounds of the invention display soft drug characteristics, i.e. they are rapidly inactivated upon entry in the systemic circulation. Therefore, they allow for reduced systemic exposure to functionally active ROCK inhibitors.

BACKGROUND OF THE INVENTION

The serine/threonine protein kinase ROCK consists in humans of two isoforms ROCK I and ROCK II. ROCK I is encoded on chromosome 18 whereas ROCK II, also called Rho-kinase, is located on chromosome 12. They both have a molecular weight close to 160 kDa. They share an overall homology of 65% while being 95% homologous in their kinase domains. Despite their sequence similarity, they differ by their tissue distributions. The highest levels of expression for ROCK I are observed in heart, lung and skeletal tissues whereas ROCK II is mostly expressed in brain. Recent data indicate that these two isoforms are partially function redundant, ROCK I being more involved in immunological events, ROCK II in smooth muscle function. The term ROCK refers to ROCK I (ROK-β, p160ROCK, or Rho-kinase β) and ROCK II (ROCK-α or Rho-kinase α).

ROCK activity has been shown to be enhanced by GTPase RhoA that is a member of the Rho (Ras homologous) GTP-binding proteins. The active GTP-bound state of RhoA interacts with Rho-binding domain (RBD) of ROCK that is located in an autoinhibitory carboxyl-terminal loop. Upon binding, the interactions between the ROCK negative regulatory domain and the kinase domain are disrupted. The process enables the kinase to acquire an open conformation in which it is fully active. The open conformation is also induced by the binding of lipid activators such as arachidonic acid to the PH domain in the kinase carboxyl-terminal domain. Another activation mechanism has been described during apoptosis and involves the cleavage of carboxyl terminus by caspase-3 and -2 (or granzyme B) for ROCK I and II, respectively.

ROCK plays an important role in various cellular functions such as smooth muscle contraction, actin cytoskeleton organization, platelet activation, downregulation of myosin phosphatase cell adhesion, -migration, -proliferation and survival, thrombin-induced responses of aortic smooth muscle cells, hypertrophy of cardiomyocytes, bronchial smooth muscle contraction, smooth muscle contraction and cytoskeletal reorganization of non-muscle cells, activation of volume-regulated anion channels, neurite retraction, wound healing, cell transformation and gene expression. ROCK also acts in several signaling pathways that are involved in auto-immunity and inflammation. ROCK has been shown to play a part in the activation of NF-κB, a critical molecule that leads to the production of TNF and other inflammatory cytokines. ROCK inhibitors are reported to act against TNF-alpha and IL-6 production in lipopolysaccharide (LPS)-stimulated THP-1 macrophages. Therefore, ROCK inhibitors provide a useful therapy to treat autoimmune and inflammatory diseases as well as oxidative stress.

ROCK also plays an important role in numerous critical cellular processes involved in angiogenesis. These include stress fiber formation, endothelial cell (EC) polarity, EC adhesion, EC motility, cytokinesis, and apoptosis. Previous studies already showed that Rho-signaling is essential for vascular endothelial growth factor (VEGF)-dependent in vitro capillary formation and in vivo angiogenesis. This suggests that Rho/ROCK inhibition may be a new way to treat angiogenesis-related disorders, such as neovascularization of the cornea or age-related macular degeneration.

In conclusion, ROCK is a major control point in smooth muscle cell function and a key signaling component involved in inflammatory processes in various inflammatory cells as well as fibrosis and remodeling in many diseased organs. In addition, ROCK has been implicated in various diseases and disorders including eye diseases; airway diseases; cardiovascular and vascular diseases; inflammatory diseases; neurological and CNS disorders: proliferative diseases; kidney diseases; sexual dysfunction; blood diseases; bone diseases; diabetes; benign prostatic hyperplasia, transplant rejection, liver disease, systemic lupus erythematosus, spasm, hypertension, chronic obstructive bladder disease, premature birth, infection, allergy, obesity, pancreatic disease and AIDS.

ROCK appears to be a relatively safe target, as exemplified by knockout models and a large number of academic studies. These KO mice data, in combination with post-marketing surveillance studies with Fasudil, a moderately potent ROCK inhibitor used for the treatment of vasospasm after subarachnoid hemorrhage, indicate that ROCK is a genuine and significant drug target.

ROCK inhibitors would be useful as therapeutic agents for the treatment of disorders implicated in the ROCK pathway. Accordingly, there is a great need to develop ROCK inhibitors that are useful in treating various diseases or conditions associated with ROCK activation, particularly given the inadequate treatments currently available for the majority of these disorders. Some non-limiting examples are glaucoma, asthma and COPD.

Glaucoma is a neurodegenerative disease that is the second most important cause of irreversible blindness. This disease is characterized by a raised intra-ocular pressure (IOP) and by progressive retinal ganglion cell apoptosis, resulting in irreversible visual field loss. Current treatment of this disease is directed towards the reduction of IOP, which is the main—but not only—risk factor for glaucoma. There is a need for improved treatment as the current therapy does only control and not cure the disease and further causes irritation, local and systemic side effects. In addition, additional positive effects, such as the anti-inflammatory and nerve regenerating components of ROCK inhibitors, would be highly preferred. Reference ROCK inhibitors, such as Y-27632 cause changes in cell shape and decrease stress fibers, focal adhesions and MLC phosphorylation in cultured human TM cells; they relax human trabecular meshwork in vitro, relax human Schlemm's canal endothelial cells in vitro and when topically applied to animals give a significant increase in trabecular outflow, resulting into a strong lowering of intra ocular pressure.

Allergic asthma is a chronic inflammatory airway disorder that results from maladaptive immune responses to ubiquitous environmental proteins in genetically susceptible persons. Despite reasonably successful therapies, the prevalence of allergic asthma increases as these therapies do not cure; there are still exacerbations and an increasing number of non-responders. New, effective and steroid-sparing treatments that tackle all components of the disease are required.

Age-related macular degeneration (AMD) is the leading cause of visual loss in the elderly population. Wet or neovascular AMD leads to rapid, devastating visual loss due to choroidal neovascularization (CNV), macular edema and photoreceptor cell death. Nowadays, anti-Vascular Endothelial Growth Factor (VEGF) therapy constitutes the first line of therapy for active CNV in wet AMD. VEGF promotes angiogenesis and vascular permeability and plays an important role in CNV formation. Different drugs aimed at blocking VEGF or its receptors have been developed. Besides neovascularization, the pathogenesis of AMD also comprises inflammation and scarring. A recent preclinical study showed that anti-VEGF treatment is restricted to reduction of angiogenesis, and can even give rise to inflammation and scarring. Another big concern is that anti-VEGF can give rise to major systemic side effects due to regression of blood vessels and neurodegeneration, as well as local side effects. So there is a need for alternative treatment modalities. Previous studies already showed that pharmacological inhibition of ROCK1 and ROCK2 by Y-27632 strongly disrupts angiogenesis and that ROCK-inhibition reduces inflammation and scarring. Therefore, ROCK-inhibitors might be an attractive and improved alternative to anti-VEGF therapies for the treatment of wet AMD.

Chronic Obstructive Pulmonary Disease (COPD) represents a group of diseases characterized by irreversible limitation of airflow, associated with abnormal inflammatory response, bronchoconstriction and remodeling and destruction of the tissue of the lung. It is one of the leading causes of death worldwide, with a steadily increasing prevalence. There is an urgent need for novel therapeutic approaches as the current regimen is inadequate. The current treatment is essentially based on bronchodilators, since glucocorticoids have limited or no effect. ROCK inhibitors could provide new treatment strategies for COPD. Reference ROCK inhibitors, such as Y-27632 relax human isolated bronchial preparations, inhibit increases in airway resistance in anaesthetised animals, potentiate relaxing effects of β-agonists in vitro and in vivo and give rapid bronchodilatation upon inhalation. In addition, ROCK inhibitors block tracheal smooth muscle contractions induced by $H_2O_2$, the clinical marker for oxidative stress. Related to airway inflammation, ROCK inhibitors counteract the increase in trans-endothelial permeability mediated by inflammatory agents, maintain the endothelial barrier integrity, inhibit the influx of eosinophils after ovalbumin challenge in vivo, protect against lung edema formation and neutrophile migration, suppress airway HR to metacholine and serotonin in allergic mice and block LPS-induced TNF release. With respect to airway fibrosis and remodeling, ROCK inhibitors block the induced migration of airway smooth muscle cells. In vitro evidences for the role of ROCK in airway remodeling were obtained in human lung carcinoma cell line, bovine tracheal smooth muscle cells and human airway smooth muscle. In vivo proof for a role of ROCK in fibrosis in general was generated with mice which exhibited attenuated myocardial fibrosis in response to the partial deletion of ROCK. The attenuation of myocardial fibrosis by Y-27632 in response to myocardial infarction and by fasudil in the case of congestive heart failure in a chronic hypertensive rat model brings additional indications of ROCK importance in remodeling. Finally, ROCK inhibitors increase apoptotic cell loss of smooth muscle cells.

Several different classes of ROCK inhibitors are known. The current focus is oncology and cardiovascular applications. Until now, the outstanding therapeutic potential of ROCK inhibitors has only been explored to a limited extent. The reason is the fact that ROCK is such a potent and widespread biochemical regulator, that systemic inhibition of ROCK leads to strong biological effects that are considered as being side effects for the treatment of most of the diseases. Indeed, the medical use of ROCK inhibitors for non-cardiological indications is hampered by the pivotal role of ROCK in the regulation of the tonic phase of smooth muscle cell contraction. Systemically available ROCK inhibitors induce a marked decrease in blood pressure. Therefore, ROCK inhibitors with different properties are highly required.

For the target specific treatment of disorders by regulating smooth muscle function and/or inflammatory processes and/or remodeling, it is highly desired to deliver a ROCK inhibitor to the target organ and to avoid significant amounts of these drugs to enter other organs. Therefore, local or topical application is desired. Typically, topical administration of drugs has been applied for the treatment of airway, eye, sexual dysfunction and skin disorders. In addition, local injection/infiltration into diseased tissues further extend the potential medical use of locally applied ROCK inhibitors. Given certain criteria are fulfilled; these local applications allow high drug concentration to be reached in the target tissue. In addition, the incorporation of ROCK inhibitors into implants and stents can further expand the medical application towards the local treatment of CV diseases such as atherosclerosis, coronary diseases and heart failure.

Despite the fact that direct local application is preferred in medical practice, there are still concerns regarding drug levels reached into the systemic circulation. For example the treatment of airway diseases by local delivery by for instance inhalation, poses the risk of systemic exposure due to large amounts entering the GI tract and/or systemic absorption through the lungs. For the treatment of eye diseases by local delivery, also significant amounts enter the GI tract and/or systemic circulation due to the low permeability of the cornea, low capacity for fluid, efficient drainage and presence of blood vessels in the eyelids. Also for dermal applications, local injections and implantable medical devices, there is a severe risk of leakage into the systemic circulation. Therefore, in addition to local application, the compounds should preferably have additional properties to avoid significant systemic exposure.

Soft drugs, also known as antedrugs, are biologically active compounds, which are designed so that they are rapidly inactivated once they enter the systemic circulation. This inactivation involves the controlled conversion of said soft drug towards a predictable metabolite displaying markedly reduced functional activity or, preferably, negligible functional activity. Inactivation can be achieved in the liver, or in the blood flow. These compounds, once applied locally to the target tissue/organ exert their desired effect locally. When they leak out of the target tissue into the systemic circulation, they are rapidly inactivated. Thus, soft drugs of choice are sufficiently stable in the target tissue/organ to exert the desired biological effect, but are rapidly degraded in the blood to biologically inactive compounds. Soft drug therefore allow for reduced systemic exposure to a functionally active drug compound. Soft drugs should not be confused with prodrugs, which undergo controlled conversion towards a functionally active metabolite and whom purpose is usually to provide increased exposure to a functionally active compound.

In view of the high potential of ROCK inhibitors for generating undesirable side effects, it will be appreciated that soft drug approaches represent an attractive way of generating ROCK inhibitors with improved properties; in particular ROCK inhibitors associated with reduced systemic exposure and therefore lower potential for undesirable side effects.

Although soft drugs represent an attractive approach for the inhibition of ROCK and the treatment of ROCK-associated diseases or conditions, the design and optimization of such compounds is not trivial. Successful soft drugs have to retain strong on-target potency and functional efficacy. They should display good stability at the intended site of action (eg eye or lung), so that a pharmacologically relevant concentration of the drug can be reached and maintained for a prolonged period of time (typically several hours) at this intended site of action. Furthermore, they should be rapidly degraded once they enter systemic circulation, so that systemic exposure and the undesired side effects associated with systemic exposure are avoided. Finally, the molecule(s) resulting from the degradation of the soft drug should display markedly reduced, preferably negligible functional activity. As a result, the design and optimization of molecules successfully combining all of these aspects represents a significant technical problem.

In conclusion, there is a continuing need to design and develop soft ROCK inhibitors for the treatment of a wide range of disease states.

The compounds described herein are soft ROCK inhibitors and solve the technical problem of successfully combining strong on-target and functional efficacy, good stability in target organs (such as, but not limited to, eye or lung) and rapid conversion in blood towards a predictable, functionally inactive species. The compounds described herein and pharmaceutically acceptable compositions thereof are useful for treating or lessening the severity of a variety of disorders or conditions associated with ROCK activation. More specifically, the compounds of the invention are preferably used in the prevention and/or treatment of at least one disease or disorder, in which ROCK is involved, such as diseases linked to smooth muscle cell function, inflammation, fibrosis, excessive cell proliferation, excessive angiogenesis, hyperreactivity, barrier dysfunction, neurodegeration and remodeling. For example, the compounds of the invention may be used in the prevention and/or treatment of diseases and disorders such as:

Eye diseases or disorders: including but not limited to retinopathy, optic neuropathy, glaucoma and degenerative retinal diseases such as macular degeneration, proliferative vitreoretinopathy, proliferative diabetic retinopathy, retinitis pigmentosa and inflammatory eye diseases, glaucoma filtration surgery failure, dry eye, allergic conjunctivitis, posterior capsule opacification, abnormalities of corneal wound healing and ocular pain.

Airway diseases; including but not limited to pulmonary fibrosis, emphysema, chronic bronchitis, asthma, fibrosis, pneumonia, cytsic fibrosis, chronic obstructive pulmonary disease (COPD); bronchitis and rhinitis and respiratory distress syndrome Throat, Nose and Ear diseases: including but not limited to sinus problems, hearing problems, toothache, tonsillitis, ulcer and rhinitis, Skin diseases: including but not limited to hyperkeratosis, parakeratosis, hypergranulosis, acanthosis, dyskeratosis, spongiosis and ulceration.

Intestinal diseases; including but not limited to inflammatory bowel disease (IBD), colitis, gastroenteritis, ileus, ileitis, appendicitis and Crohn's disease.

Cardiovascular and vascular diseases: including but not limited to, pulmonary hypertension and pulmonary vasoconstriction.

Inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis.

Neurological disorders: including but not limited to neuropathic pain. The present compounds are therefore suitable for preventing neurodegeneration and stimulating neurogeneration in various neurological disorders.

Proliferative diseases: such as but not limited to cancer of, breast, colon, intestine, skin, head and neck, nerve, uterus, kidney, lung, ovary, pancreas, prostate, or thyroid gland; Castleman disease; sarcoma; malignoma; and melanoma.

Kidney diseases: including but not limited to renal fibrosis or renal dysfunction Sexual dysfunction: is meant to include both male and female sexual dysfunction caused by a defective vasoactive response. The soft ROCK inhibitors of the present invention may also be used to treat sexual dysfunction arising from a variety of causes. For example, in an embodiment, the soft ROCK inhibitors may be used to treat sexual dysfunction associated with hypogonadism and more particularly, wherein the hypogonadism is associated with reduced levels of androgen hormones. In another embodiment, the soft ROCK inhibitors may be used to treat sexual dysfunction associated with a variety of causes including, but not limited to, bladder disease, hypertension, diabetes, or pelvic surgery. In addition, the soft ROCK inhibitors may be used to treat sexual dysfunction associated with treatment using certain drugs, such as drugs used to treat hypertension, depression or anxiety.

Bone diseases: including but not limited to osteoporosis and osteoarthritis

In addition, the compounds of the invention may be used in the prevention and/or treatment of diseases and disorders such as benign prostatic hyperplasia, transplant rejection, spasm, chronic obstructive bladder disease, and allergy.

SUMMARY OF THE INVENTION

We have surprisingly found that the compounds described herein act as inhibitors of ROCK, in particular as soft ROCK inhibitors. Compared to prior art known ROCK inhibitors, such as for example described in WO2012/015760, WO2008/077057, WO2010/065782, WO2009/158587, US2009/0325959, US2009/325960, Iwakubo et al. (*Bioorg. Med. Chem.*, 2007, 15, 350-364 & *Bioorg. Med. Chem.*, 2007, 15, 1022-1033) and WO2001/56988, the compounds of the present invention differ in that they are very rapidly converted into predictable, functionally inactive compounds when entering systemic circulation, yet retain good stability in target organs. Compound inactivation can occur in the liver, but is preferentially achieved directly in the blood flow, through blood enzymes, for example carboxylic ester hydrolases (EC 3.1.1) such as Cholinesterases, Paraoxonase 1 (PON1) or plasma proteins displaying pseudoesterase activity such as Human serum albumin. The compounds of the present invention therefore solve the technical problem of successfully combining on-target potency (inhibitory activity against ROCK) and functional efficacy, good stability in target organs and rapid conversion in blood towards a predictable, functionally inactive species. As a result, the compounds of the invention can achieve a desired pharmacological effect through inhibition of ROCK at the intended site of action (e.g. eye or lung), while avoiding a systemic inhibition of ROCK that would create potential for side effects.

Carboxylic ester hydrolases (EC 3.1.1) represent a large group of enzymes involved in the degradation of carboxylic esters into alcohols and carboxylic acids. As such, enzymes displaying this catalytic activity are of potential interest for the design of soft kinase inhibitors. EC 3.1.1 includes the following sub-classes: EC 3.1.1.1 carboxylesterase, EC 3.1.1.2 arylesterase, EC 3.1.1.3 triacylglycerol lipase, EC 3.1.1.4 phospholipase A2, EC 3.1.1.5 lysophospholipase, EC 3.1.1.6 acetylesterase, EC 3.1.1.7 acetylcholinesterase, EC 3.1.1.8 cholinesterase, EC 3.1.1.10 tropinesterase, EC 3.1.1.11 pectinesterase, EC 3.1.1.13 sterol esterase, EC 3.1.1.14 chlorophyllase, EC 3.1.1.15 L-arabinonolactonase, EC 3.1.1.17 gluconolactonase, EC 3.1.1.19 uronolactonase, EC 3.1.1.20 tannase, EC 3.1.1.21 retinyl-palmitate esterase, EC 3.1.1.22 hydroxybutyrate-dimer hydrolase, EC 3.1.1.23 acylglycerol lipase, EC 3.1.1.24 3-oxoadipate enol-lactonase, EC 3.1.1.25 1,4-lactonase, EC 3.1.1.26 galactolipase, EC 3.1.1.27 4-pyridoxolactonase, EC 3.1.1.28 acylcarnitine hydrolase, EC 3.1.1.29 aminoacyl-tRNA hydrolase, EC 3.1.1.30 D-arabinonolactonase, EC 3.1.1.31 6-phosphogluconolactonase, EC 3.1.1.32 phospholipase A1, EC 3.1.1.33 6-acetylglucose deacetylase, EC 3.1.1.34 lipoprotein lipase, EC 3.1.1.35 dihydrocoumarin hydrolase, EC 3.1.1.36 limonin-D-ring-lactonase, EC 3.1.1.37 steroid-lactonase, EC 3.1.1.38 triacetate-lactonase, EC 3.1.1.39 actinomycin lactonase, EC 3.1.1.40 orsellinate-depside hydrolase, EC 3.1.1.41 cephalosporin-C deacetylase, EC 3.1.1.42 chlorogenate hydrolase, EC 3.1.1.43 α-amino-acid esterase, EC 3.1.1.44 4-methyloxaloacetate esterase, EC 3.1.1.45 carboxymethylenebutenolidase, EC 3.1.1.46 deoxylimonate A-ring-lactonase, EC 3.1.1.47 1-alkyl-2-acetylglycerophosphocholine esterase, EC 3.1.1.48 fusarinine-C ornithinesterase, EC 3.1.1.49 sinapine esterase, EC 3.1.1.50 wax-ester hydrolase, EC 3.1.1.51 phorbol-diester hydrolase, EC 3.1.1.52 phosphatidylinositol deacylase, EC 3.1.1.53 sialate O-acetylesterase, EC 3.1.1.54 acetoxybutynylbithiophene deacetylase, EC 3.1.1.55 acetylsalicylate deacetylase, EC 3.1.1.56 methylumbelliferyl-acetate deacetylase, EC 3.1.1.57 2-pyrone-4,6-dicarboxylate lactonase, EC 3.1.1.58 N-acetylgalactosaminoglycan deacetylase, EC 3.1.1.59 juvenile-hormone esterase, EC 3.1.1.60 bis(2-ethylhexyl)phthalate esterase, EC 3.1.1.61 protein-glutamate methylesterase, EC 3.1.1.63 11-cis-retinyl-palmitate hydrolase, EC 3.1.1.64 all-trans-retinyl-palmitate hydrolase, EC 3.1.1.65 L-rhamnono-1,4-lactonase, EC 3.1.1.66 5-(3,4-diacetoxybut-1-ynyl)-2,2'-bithiophene deacetylase, EC 3.1.1.67 fatty-acyl-ethyl-ester synthase, EC 3.1.1.68 xylono-1,4-lactonase, EC 3.1.1.70 cetraxate benzylesterase, EC 3.1.1.71 acetylalkylglycerol acetylhydrolase, EC 3.1.1.72 acetylxylan esterase, EC 3.1.1.73 feruloyl esterase, EC 3.1.1.74 cutinase, EC 3.1.1.75 poly(3-hydroxybutyrate) depolymerase, EC 3.1.1.76 poly(3-hydroxyoctanoate) depolymerase, EC 3.1.1.77 acyloxyacyl hydrolase, EC 3.1.1.78 polyneuridine-aldehyde esterase, EC 3.1.1.79 hormone-sensitive lipase, EC 3.1.1.80 acetylajmaline esterase, EC 3.1.1.81 quorum-quenching N-acyl-homoserine lactonase, EC 3.1.1.82 pheophorbidase, EC 3.1.1.83 monoterpene ε-lactone hydrolase, EC 3.1.1.84 cocaine esterase, EC 3.1.1.85 mannosylglycerate hydrolases.

Cholinesterases are enzymes that are primarily known for their role in the degradation of the neurotransmitter acetylcholine. Acetylcholinesterase (EC 3.1.1.7) is also known as Choline esterase I, true cholinesterase, RBC cholinesterase, erythrocyte cholinesterase, or acetylcholine acetylhydrolase. As suggested by some of its alternative names, acetylcholinesterase is not only found in brain, but also in the erythrocyte fraction of blood. In addition to its action on acetylcholine, acetylcholinesterase hydrolyzes a variety of acetic esters, and also catalyzes transacetylations. Acetylcholinesterase usually displays a preference for substrates with short acid chains, as the acetyl group of acetylcholine. Butyrylcholinesterase (EC 3.1.1.8) is also known as benzoylcholinesterase, choline esterase II, non-specific cholinesterase, pseudocholinesterase, plasma cholinesterase or acylcholine acylhydrolase, While being found primarily in liver, butyrylcholinesterase is also present in plasma. As indicated by some of its alternative names, it is less specific than acetylcholinesterase and will typically carry out the hydrolysis of substrates with larger acid chains (such as the butyryl group of butyrylcholine or the benzoyl group of benzolylcholine) at a faster rate than acetylcholinesterase. In addition to its action on acetylcholine, butyrylcholinesterase is known to participate in the metabolism of several ester drugs, such as procaine.

Carboxylesterases (CES) represent a multigene family and show ubiquitous expression profiles, with high levels in liver, intestine and lungs. A majority of carboxylesterases can be classified either in carboxylesterase 1 (CES 1) or carboxylesterase 2 (CES2) families. Interestingly, these different CES families show differences in tissue distribution and substrate specificity. Human CES1 is widely distributed in many tissues, but is found in low levels in the intestine. CES1 preferentially hydrolyzes esters with relatively small alcohol groups and larger acid groups. As a typical example, hCES1 preferentially catalyzes the hydrolysis of the methyl ester of cocaine. Human CES2 is predominantly found in intestine, liver and kidney. CES2 preferentially hydrolyzes esters with smaller alcohol groups, and larger acid groups. As a typical example, human CES2 catalyzes the hydrolysis of the benzoyl ester of cocaine. Another interesting observation about CES enzymes is the lack of carboxylesterase activity in human plasma. Overall, carboxylesterases can play a major role in the bioconversion of ester-containing drugs and xenobiotics.

Human serum albumin (HSA) is a major component of blood plasma, accounting for approximately 60% of all plasma proteins. HSA has been found to catalyze the hydrolysis of various compounds such as aspirin, cinnamoylimidazole, p-nitrophenyl acetate, organophosphate insecticides, fatty acid esters or nicotinic esters. HSA displays multiple nonspecific catalytic sites in addition to its primary reactive site. The catalytic efficiency of these sites is however low, and HSA has often been described not as a true esterase, but as a pseudoesterase, In spite of its low catalytic efficiency, HSA can still play a significant role in the metabolism of drug-like compounds, because of its high concentration in plasma.

It will be understood by those skilled in the art that a major technical problem in the design of soft drugs, including soft ROCK inhibitors, is to successfully combine strong on-target potency and functional activity, good stability in the target organ and rapid degradation in the systemic circulation, towards a functionally inactive species. In order to produce the desired effect(s) in the target organ, soft ROCK inhibitors should achieve a pharmacologically relevant concentration in said target organ and maintain this concentration during a prolonged period of time, typically several hours. In order to avoid systemic inhibition of ROCK, which could potentially lead to undesired effects, soft ROCK inhibitors should be rapidly degraded once entering the systemic circulation, before they can build up a pharmacologically relevant concentration in the blood flow or in non-target organs.

It will also be understood by those skilled in the art that inhibition of ROCK results from recognition (complementary interactions) between ROCK and the soft ROCK inhibitor, while inactivation of the soft ROCK inhibitor in liver or the blood flow results from said soft ROCK inhibitor being recognized as a substrate by one or more liver or blood enzymes, for instance carboxylic ester hydrolases (EC 3.1.1). As these two recognition processes involve independent macromolecules (ROCK and the hydrolase(s)) and therefore independent ligand-binding sites, the structural features governing such recognition processes are also independent from each other and are not necessarily compatible. It will therefore be understood that the inhibitory activity of a chemical compound against ROCK is in no way predictive of its (in) stability in systemic circulation.

As discussed hereinabove, a successful soft ROCK inhibitor simultaneously needs to display low stability in the systemic circulation, but also good stability in the target organ. It will be understood by those skilled in the art that such a difference of stability between different organs and fluids can result from different enzymes (in particular esterases) being present in these tissues or fluids, from different expression levels ("concentrations") of the same enzyme, or from both. It will also be understood that each additional enzyme, including esterases, present in the organ or fluid represents a new ligand-binding site with its own set of rules governing recognition as a substrate. Such rules are not necessarily compatible with each other, usually resulting in most enzymes displaying some degree of substrate specificity. In order to achieve acceptable stability in the target organ, a successful soft ROCK inhibitor should therefore avoid, at least up to a certain point, being recognized as a substrate by the degrading enzymes, including carboxylic ester hydrolases, which are present in significant quantities in the target organ. Once again, it will be understood that the inhibitory activity of a chemical compound against ROCK is in no way predictive of its (in)stability in the target organ. Additionally, it will be understood that as the potential degradation mechanisms in liver, blood flow and target organ can involve different enzymes; (in)stability in the liver or blood flow is in no way predictive of (in)stability in the target organ.

In view of the above, it will be understood that the design of a soft ROCK inhibitor displaying the appropriate activity and stability profile represents a significant technical problem to be solved. In particular, it will be understood that inhibitory activity against ROCK and stability in liver, blood flow or target organ are governed by independent sets of structural rules, making the design of a successful soft ROCK inhibitor non-obvious.

It will also be understood by those skilled in the art that soft drugs and prodrugs represent opposite approaches in their conception and purpose, even though both approaches involve the controlled and predictable metabolism of an administered compound. Indeed, a soft drug is a chemical compound with strong functional activity, which undergoes controlled metabolism towards a functionally inactive and therefore nontoxic species. The purpose of a soft drug is to decrease systemic exposure to a functionally active compound and to direct the metabolism and elimination of this drug compound towards a predictable route, leading to a functionally inactive, nontoxic metabolite. By opposition, a prodrug is a chemical compound that does not necessarily possess functional activity, but undergoes controlled metabolism towards a functionally active compound. The purpose of a prodrug is to increase exposure to a functionally active compound, for example because the prodrug displays higher cellular permeability, higher bioavailability, or allows the sustained release of a functionally active compound which is otherwise rapidly cleared from the blood flow.

Unless a context dictates otherwise, asterisks are used herein to indicate the point at which a mono- or bivalent radical depicted is connected to the structure to which it relates and of which the radical forms part.

Viewed from a first aspect, the invention provides a compound of Formula I or a stereoisomer, tautomer, racemic, salt, hydrate, or solvate thereof,

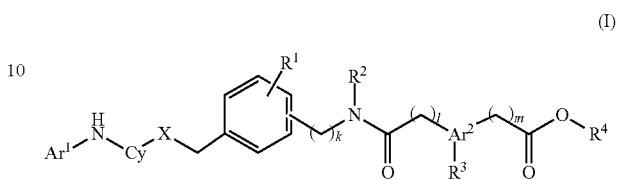

Wherein
$Ar^1$ is selected from the group comprising

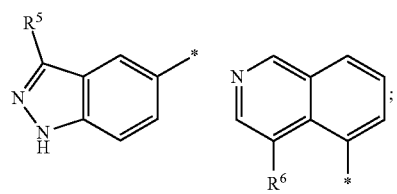

$Ar^2$ represents an aryl or heteroaryl;
Cy is a $C_{3-15}$cycloalkyl wherein optionally one carbon atom is replaced by a nitrogen atom;
X is a direct bond, —NH— or —N($C_{1-6}$alkyl)-;
$R^1$ is selected from the group comprising hydrogen, halogen, $C_{1-6}$ alkyl, and $C_{1-6}$ alkoxyl;
$R^2$ is selected from the group comprising hydrogen and $C_{1-3}$ alkyl;
$R^3$ is selected from the group comprising hydrogen, halogen, $C_{1-6}$ alkyl, and $C_{1-6}$ alkoxyl;
$R^4$ is an optionally substituted group selected from the group comprising $C_{1-20}$alkyl, $C_{1-20}$alkenyl, $C_{1-20}$alkynyl, $C_{3-15}$cycloalkyl, aryl, heterocyclyl, and heteroaryl;
$R^5$ is selected from hydrogen, $C_{1-6}$alkyl and $NH_2$;
$R^6$ is selected from hydrogen, halo and $C_{1-6}$alkyl;
k is an integer from 0 to 3;
l is an integer from 0 to 3;
m is an integer from 0 to 3.

As can be seen from the above, all compounds of formula I contain at least one ester. Hydrolysis of this ester through carboxylic ester hydrolases results in compounds with reduced on-target potency and/or functional activity. Compounds of formula I thereby qualify as soft ROCK inhibitors.

Viewed from a further aspect, the invention provides the use of a compound of the invention, or a composition comprising such a compound, for inhibiting the activity of at least one kinase, in vitro or in vivo.

Viewed from a further aspect, the invention provides the use of a compound of the invention, or a composition comprising such a compound, for inhibiting the activity of at least one ROCK kinase, for example ROCKII and/or ROCKI isoforms; in vitro or in vivo.

Viewed from a further aspect, the invention provides a pharmaceutical and/or veterinary composition comprising a compound of the invention.

Viewed from a still further aspect, the invention provides a compound of the invention for use in human or veterinary medicine.

Viewed from a still further aspect, the invention provides the use of a compound of the invention in the preparation of a medicament for the prevention and/or treatment of at least one disease and/or disorder selected from the group comprising eye diseases; airway diseases; throat, nose and ear diseases; intestinal diseases; cardiovascular and vascular diseases; inflammatory diseases; neurological and CNS disorders: proliferative diseases; kidney diseases; sexual dysfunction; bone diseases; benign prostatic hyperplasia, transplant rejection, spasm, chronic obstructive bladder disease, and allergy.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

FIG. 1: Concentration-response curves for compound 32 (diamonds) and its metabolite Met1 (hollow circles) in the MLC phosphorylation assay; illustrating the difference of functional activity between parent compound and metabolite. Relative MLC phosphorylation is measured with respect to untreated cells (Positive control, 1.0) and cells treated with 100 μM Y-27632 (Negative control, 0.0). Each data point is the average of three measurements. 95% CI are provided as dotted lines for both curves.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

Undefined (racemic) asymmetric centers that may be present in the compounds of the present invention are interchangeably indicated by drawing a wavy bonds or a straight bond in order to visualize the undefined steric character of the bond.

As already mentioned hereinbefore, in a first aspect the present invention provides compounds of Formula I

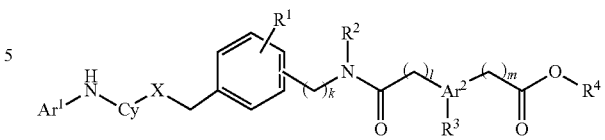

Wherein $Ar^1$, $Ar^2$, X, Cy, X, $R^1$, $R^2$, $R^3$, $R^4$, k, l, m are as defined hereinbefore, including the stereoisomeric forms, solvates, and pharmaceutically acceptable addition salts thereof.

When describing the compounds of the invention, the terms used are to be construed in accordance with the following definitions, unless a context dictates otherwise:

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 20 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3, or 4 substituents or 1 to 2 substituents; in particular one substituent) at any available point of attachment. Non-limiting examples of such substituents include halo, hydroxyl, oxo, carbonyl, nitro, amino, amido, oxime, imino, azido, hydrazino, cyano, aryl, heteroaryl, cycloalkyl, heterocyclyl, acyl, alkylamino, alkoxy, haloalkoxy, haloalkyl, thiol, alkylthio, carboxylic acid, acylamino, alkyl esters, carbamate, thioamido, urea, sulfonamido and the like. Preferably, such substituents are selected from halo, hydroxyl, nitro, amino, cyano, aryl (in particular phenyl), cycloalkyl, heterocyclyl (in particular pyrrolidine, oxolane, thiolane or $Het^1$ as described hereinbelow; more in particular pyrrolidine or oxolane), and alkoxy. More preferably, the substituents are selected from hydroxyl, aryl (in particular phenyl), cycloalkyl, heterocyclyl (in particular pyrrolidine, oxolane, thiolane or $Het^1$ as described hereinbelow; more in particular pyrrolidine or oxolane), and alkoxy.

The term "alkenyl", as used herein, unless otherwise indicated, means straight-chain, cyclic, or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like. An optionally substituted alkenyl refers to an alkenyl having optionally one or more substituents (for example 1, 2, 3 or 4), selected from those defined above for substituted alkyl.

The term "alkynyl", as used herein, unless otherwise indicated, means straight-chain or branched-chain hydrocarbon radicals containing at least one carbon-carbon triple bond. Examples of alkynyl radicals include ethynyl, propynyl, butynyl, pentynyl, hexynyl, and the like. An optionally substituted alkynyl refers to an alkynyl having optionally one or more substituents (for example 1, 2, 3 or 4), selected from those defined above for substituted alkyl.

The term "cycloalkyl" by itself or as part of another substituent is a cyclic alkyl group, that is to say, a monovalent, saturated, or unsaturated hydrocarbyl group having 1, 2, or 3 cyclic structure. Cycloalkyl includes all saturated or partially saturated (containing 1 or 2 double bonds) hydrocarbon groups containing 1 to 3 rings, including monocyclic, bicyclic, or polycyclic alkyl groups. Cycloalkyl groups may comprise 3 or more carbon atoms in the ring and generally, according to this invention comprise from 3 to 15 atoms. The further rings of multi-ring cycloalkyls may be either fused, bridged and/or joined through one or more spiro atoms. Cycloalkyl groups may also be considered to be a subset of homocyclic rings discussed hereinafter. Examples of cycloalkyl groups include but are not limited to cyclopropyl, cyclobutyl, cyclopentyl, cyclohexyl, cycloheptyl, cyclooctyl, cyclononyl, adamantanyl, bicyclo(2.2.1)heptanyl and cyclodecyl with cyclopropyl, cyclopentyl, cyclohexyl, adamantanyl, and bicyclo(2.2.1)heptanyl being particularly preferred. An "optionally substituted cycloalkyl" refers to a cycloalkyl having optionally one or more substituents (for example 1 to 3 substituents, for example 1, 2, 3 or 4 substituents), selected from those defined above for substituted alkyl. When the suffix "ene" is used in conjunction with a cyclic group, hereinafter also referred to as "Cycloalkylene", this is intended to mean the cyclic group as defined herein having two single bonds as points of attachment to other groups. Cycloalkylene groups of this invention preferably comprise the same number of carbon atoms as their cycloalkyl radical counterparts.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkenyl groups as defined above and alkynyl groups as defined above, respectively, are divalent radicals having single bonds for attachment to two other groups, they are termed "alkenylene" and "alkynylene" respectively.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom, preferably a common carbon atom. To illustrate this applying the asterisk nomenclature of this invention, a $C_3$ alkylene group may be for example *—$CH_2CH_2$ $CH_2$—*, *—$CH(-CH_2CH_3)$—*, or *—$CH_2CH$ (—$CH_3$)—*. Likewise a $C_3$ cycloalkylene group may be:

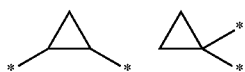

Where a cycloalkylene group is present, this is preferably a $C_3$-$C_6$ cycloalkylene group, more preferably a $C_3$ cycloalkylene (i.e. cyclopropylene group) wherein its connectivity to the structure of which it forms part is through a common carbon atom. Cycloalkylene and alkylene biradicals in compounds of the invention may be, but preferably are not, substituted.

The terms "heterocyclyl" or "heterocyclo" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. An optionally substituted heterocyclyl refers to a heterocyclyl having optionally one or more substituents (for example 1 to 4 substituents, or for example 1, 2, 3 or 4), selected from those defined for substituted aryl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl.

The term "aryl" as used herein refers to a polyunsaturated, aromatic hydrocarbyl group having a single ring (i.e. phenyl) or multiple aromatic rings fused together (e.g. naphthalene or anthracene) or linked covalently, typically containing 6 to 10 atoms; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1- 2-, 3-, 4-, or 5-acenaphtylenyl, 3-, 4-, or 5-acenaphtenyl, 1-, 2-, 3-, 4-, or 10-phenanthryl, 1- or 2-pentalenyl, 1,2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment. Non-limiting examples of such substituents are selected from halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —SO₂—NH₂, aryl, heteroaryl, aralkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —SO₂R$^a$, alkylthio, carboxyl, and the like, wherein R$^a$ is alkyl or cycloalkyl. Preferably, such substituents are selected from halogen, hydroxyl, nitro, amino, cyano, alkyl (in particular C$_{1-6}$alkyl; more in particular methyl), alkylamino, alkoxy, and haloalkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, benzopyranyl, 1(4H)-benzopyranyl, 1(2H)-benzopyranyl, 3,4-dihydro-1(2H)-benzopyranyl, 3,4-dihydro-1(2H)-benzopyranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

The term "pyrrolyl" (also called azolyl) as used herein includes pyrrol-1-yl, pyrrol-2-yl and pyrrol-3-yl. The term "furanyl" (also called "furyl") as used herein includes furan-2-yl and furan-3-yl (also called furan-2-yl and furan-3-yl). The term "thiophenyl" (also called "thienyl") as used herein includes thiophen-2-yl and thiophen-3-yl (also called thien-2-yl and thien-3-yl). The term "pyrazolyl" (also called 1H-pyrazolyl and 1,2-diazolyl) as used herein includes pyrazol-1-yl, pyrazol-3-yl, pyrazol-4-yl and pyrazol-5-yl. The term "imidazolyl" as used herein includes imidazol-1-yl, imidazol-2-yl, imidazol-4-yl and imidazol-5-yl. The term "oxazolyl" (also called 1,3-oxazolyl) as used herein includes oxazol-2-yl; oxazol-4-yl and oxazol-5-yl. The term "isoxazolyl" (also called 1,2-oxazolyl), as used herein includes isoxazol-3-yl, isoxazol-4-yl, and isoxazol-5-yl. The term "thiazolyl" (also called 1,3-thiazolyl), as used herein includes thiazol-2-yl, thiazol-4-yl and thiazol-5-yl (also called 2-thiazolyl, 4-thiazolyl and 5-thiazolyl). The term "isothiazolyl" (also called 1,2-thiazolyl) as used herein includes isothiazol-3-yl, isothiazol-4-yl and isothiazol-5-yl. The term "triazolyl" as used herein includes 1H-triazolyl and 4H-1,2,4-triazolyl, "1H-triazolyl" includes 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl and 1H-1,2,4-triazol-5-yl. "4H-1,2,4-triazolyl" includes 4H-1,2,4-triazol-4-yl, and 4H-1,2,4-triazol-3-yl. The term "oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl. The term "thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl. The term "tetrazolyl" as used herein includes 1H-tetrazol-1-yl, 1H-tetrazol-5-yl, 2H-tetrazol-2-yl, and 2H-tetrazol-5-yl. The term "oxatriazolyl" as used herein includes 1,2,3,4-oxatriazol-5-yl and 1,2,3,5-oxatriazol-4-yl. The term "thiatriazolyl" as used herein includes 1,2,3,4-thiatriazol-5-yl and 1,2,3,5-thiatriazol-4-yl. The term "pyridinyl" (also called "pyridyl") as used herein includes pyridin-2-yl, pyridin-3-yl and pyridin-4-yl (also called 2-pyridyl, 3-pyridyl and 4-pyridyl). The term "pyrimidyl" as used herein includes pyrimid-2-yl, pyrimid-4-yl, pyrimid-5-yl and pyrimid-6-yl. The term "pyrazinyl" as used herein includes pyrazin-2-yl and pyrazin-3-yl. The term "pyridazinyl" as used herein includes pyridazin-3-yl and pyridazin-4-yl. The term "oxazinyl" (also called "1,4-oxazinyl") as used herein includes 1,4-oxazin-4-yl and 1,4-oxazin-5-yl. The term "dioxinyl" (also called "1,4-dioxinyl") as used herein includes 1,4-dioxin-2-yl and 1,4-dioxin-3-yl. The term "thiazinyl" (also called "1,4-thiazinyl") as used herein includes 1,4-thiazin-2-yl, 1,4-thiazin-3-yl, 1,4-thiazin-4-yl, 1,4-thiazin-5-yl and 1,4-thiazin-6-yl. The term "triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl. The term "imidazo[2,1-b][1,3]thiazolyl" as used herein includes imidazo[2,1-b][1,3]thiazoi-2-yl, imidazo[2,1-b][1,3]thiazol-3-yl, imidazo[2,1-b][1,3]thiazol-5-yl and imidazo[2,1-b][1,3]thiazol-6-yl. The term "thieno[3,2-b]furanyl" as used herein includes thieno[3,2-b]furan-2-yl, thieno[3,2-b]furan-3-yl, thieno[3,2-b]furan-4-yl, and thieno[3,2-b]furan-5-yl. The term "thieno[3,2-b]thiophenyl" as used herein includes thieno[3,2-b]thien-2-yl, thieno[3,2-b]thien-3-yl, thieno[3,2-b]thien-5-yl and thieno[3,2-b]thien-6-yl. The term "thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl. The term "thieno[2,3-d]imidazolyl" as used herein includes thieno[2,3-d]imidazol-2-yl, thieno[2,3-d]imidazol-4-yl and thieno[2,3-d]imidazol-5-yl. The term "tetrazolo[1,5-a]pyridinyl" as used herein includes tetrazolo[1,5-a]pyridine-5-yl, tetrazolo[1,5-a]pyridine-6-yl, tetrazolo[1,5-a]pyridine-7-yl, and tetrazolo[1,5-a]pyridine-8-yl. The term "indolyl" as used herein includes indol-1-yl, indol-2-yl, indol-3-yl,-indol-4-yl, indol-5-yl, indol-6-yl and indol-7-yl. The term "indolizinyl" as used herein includes indolizin-1-yl, indolizin-2-yl, indolizin-3-yl, indolizin-5-yl, indolizin-6-yl, indolizin-7-yl, and indolizin-8-yl. The term "isoindolyl" as used herein includes isoindol-1-yl, isoindol-2-yl, isoindol-3-yl, isoindol-4-yl, isoindol-5-yl, isoindol-6-yl and isoindol-7-yl. The term "benzofuranyl" (also called benzo[b]furanyl) as used herein includes benzofuran-2-yl, benzofuran-3-yl, benzofuran-4-yl, benzofuran-5-yl, benzofuran-6-yl and benzofuran-7-yl. The term "isobenzofuranyl" (also called benzo[c]furanyl) as used herein includes isobenzofuran-1-yl, isobenzofuran-3-yl, isobenzofuran-4-yl, isobenzofuran-5-yl, isobenzofuran-6-yl and isobenzofuran-7-yl. The term "benzothiophenyl" (also called benzo[b]thienyl) as used herein includes 2-benzo[b]thiophenyl, 3-benzo[b]thiophenyl, 4-benzo[b]thiophenyl, 5-benzo[b]thiophenyl, 6-benzo[b]thiophenyl and -7-benzo[b]thiophenyl (also called benzothien-2-yl, benzothien-3-yl, benzothien-4-yl, benzothien-5-yl, benzothien-6-yl and benzothien-7-yl). The term "isobenzothiophenyl" (also called benzo[c]thienyl) as used herein includes isobenzothien-1-yl, isobenzothien-3-yl, isobenzothien-4-yl, isobenzothien-5-yl, isobenzothien-6-yl and isobenzothien-7-yl. The term "indazolyl" (also called 1H-indazolyl or 2-azaindolyl) as used herein includes 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, and 2H-indazol-7-yl.

The term "benzimidazolyl" as used herein includes benzimidazol-1-yl, benzimidazol-2-yl, benzimidazol-4-yl, benzimidazol-5-yl, benzimidazol-6-yl and benzimidazol-7-yl. The term "1,3-benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl. The term "1,2-benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl. The term "2,1-benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl. The term "1,3-benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl. The term "1,2-benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl. The term "2,1-benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl. The term "benzotriazolyl" as used herein includes benzotriazol-1-yl, benzotriazol4-yl, benzotriazol-5-yl, benzotriazol-6-yl and benzotriazol-7-yl. The term "1,2,3-benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl. The term "2,1,3-benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl. The term "1,2,3-benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl. The term "2,1,3-benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl. The term "thienopyridinyl" as used herein includes thieno[2,3-b]pyridinyl, thieno[2,3-c]pyridinyl, thieno[3,2-c]pyridinyl and thieno[3,2-b]pyridinyl. The term "purinyl" as used herein includes purin-2-yl, purin-6-yl, burin-7-yl and purin-8-yl. The term "imidazo[1,2-a]pyridinyl", as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl. The term "1,3-benzodioxolyl", as used herein includes 1,3-benzodioxol-4-yl, 1,3-benzodioxol-5-yl, 1,3-benzodioxol-6-yl, and 1,3-benzodioxol-7-yl. The term "quinolinyl" as used herein includes quinolin-2-yl, quinolin-3-yl, quinolin-4-yl, quinolin-5-yl, quinolin-6-yl, quinolin-7-yl and quinolin-8-yl. The term "isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl. The term "cinnolinyl" as used herein includes cinnolin-3-yl, cinnolin-4-yl, cinnolin-5-yl, cinnolin-6-yl, cinnolin-7-yl and cinnolin-8-yl. The term "quinazolinyl" as used herein includes quinazolin-2-yl, quiriazolin-4-yl, quinazolin-5-yl, quinazolin-6-yl, quinazolin-7-yl and quinazolin-8-yl. The term "quinoxalinyl" as used herein includes quinoxalin-2-yl, quinoxalin-5-yl, and quinoxalin-6-yl. The term "7-azaindolyl" as used herein refers to 1H-Pyrrolo[2,3-b]pyridinyl and includes 7-azaindol-1-yl, 7-azaindol-2-yl, 7-azaindol-3-yl, 7-azaindol-4-yl, 7-azaindol-5-yl, 7-azaindol-6-yl. The term "6-azaindolyl" as used herein refers to 1H-Pyrrolo[2,3-c]pyridinyl and includes 6-azaindol-1-yl, 6-azaindol-2-yl, 6-azaindol-3-yl, 6-azaindol-4-yl, 6-azaindol-5-yl, 6-azaindol-7-yl. The term "5-azaindolyl" as used herein refers to 1H-Pyrrolo[3,2-c]pyridinyl and includes 5-azaindol-1-yl, 5-azaindol-2-yl, 5-azaindol-3-yl, 5-azaindol-4-yl, 5-azaindol-6-yl, 5-azaindol-7-yl. The term "4-azaindolyl" as used herein refers to 1H-Pyrrolo[3,2-b]pyridinyl and includes 4-azaindol-1-yl, 4-azaindol-2-yl, 4-azaindol-3-yl, 4-azaindol-5-yl, 4-azaindol-6-yl, 4-azaindol-7-yl.

For example, non-limiting examples of heteroaryl can be 2- or 3-furyl, 2- or 3-thienyl, 1-, 2- or 3-pyrrolyl, 1-, 2-, 4- or 5-imidazolyl, 1-, 3-, 4- or 5-pyrazolyl, 3-, 4- or 5-isoxazolyl, 2-, 4- or 5-oxazolyl, 3-, 4- or 5-isothiazolyl, 2-, 4- or 5-thiazolyl, 1,2,3-triazol-1-, -4- or -5-yl, 1,2,4-triazol-1-, -3-, -4- or -5-yl, 1H-tetrazol-1-, or -5-yl, 2H-tetrazol-2-, or -5-yl, 1,2,3-oxadiazol-4- or -5-yl, 1,2,4-oxadiazol-3- or -5-yl, 1,2,5-oxadiazolyl, 1,3,4-oxadiazolyl, 1,2,3-thiadiazol-4- or -5-yl, 1,2,4-thiadiazol-3- or -5-yl, 1,2,5-thiadiazol-3- or -4-yl, 1,3,4-thiadiazolyl, 1- or 5-tetrazolyl, 2-, 3- or 4-pyridyl, 4-pyridazinyl, 2-, 4-, 5- or 6-pyrimidyl, 2-, 3-, 4-, 5- 6-2H-thiopyranyl, 2-, 3- or 4-4H-thiopyranyl, 4-azaindol-1-, 2-, 3-, 5-, or 7-yl, 5-azaindol-1-, or 2-, 3-, 4-, 6-, or 7-yl, 6-azaindol-1,2-, 3-, 4-, 5-, or 7-yl, 7-azaindol-1-, 2-, 3-, 4,5-, or 6-yl, 2-, 3-, 4-, 5-, 6- or 7-benzofuryl, 1-, 3-, 4- or 5-isobenzofuryl, 2-, 3-, 4-, 5-, 6- or 7-benzothienyl, 1-, 3-, 4- or 5-isobenzothienyl, 1-, 2-, 3-, 4-, 5-, 6- or 7-indolyl, 2- or 3-pyrazinyl, 1,4-oxazin-2- or -3-yl, 1,4-dioxin-2- or -3-yl, 1,4-thiazin-2- or -3-yl, 1,2,3-triazinyl, 1,2,4-triazinyl, 1,3,5-triazin-2-, -4- or -6-yl, thieno[2,3-b]furan-2-, -3-, -4-, or -5-yl, benzimidazol-1-yl, -2-yl, -4-yl, -5-yl, -6-yl, or -7-yl, 1-, 3-, 4-, 5-, 6- or 7-benzopyrazolyl, 3-, 4-, 5-, 6- or 7-benzisoxazolyl, 2-, 4-, 5-, 6- or 7-benzoxazolyl, 3-, 4-, 5-, 6- or 7-benzisothiazolyl, 1,3-benzothiazol-2-yl, -4-yl, -5-yl, -6-yl or -7-yl, 1,3-benzodioxol-4-yl, -5-yl, -6-yl, or -7-yl, benzotriazol-1-yl, -4-yl, -5-yl, -6-yl or -7-yl1, 2-thianthrenyl, 3-, 4- or 5-isobenzofuranyl, 1-, 2-, 3-, 4- or 9-xanthenyl, 1-, 2-, 3- or 4-phenoxathiinyl, 2-, 3-pyrazinyl, 1-, 2-, 3-, 4-, 5-, 6-, 7- or 8-indolizinyl, 2-, 3-, 4- or 5-isoindolyl, 1H-indazol-1-yl, 3-yl, -4-yl, -5-yl, -6-yl, or -7-yl, 2H-indazol-2-yl, 3-yl, -4-yl, -5-yl, -6-yl, or -7-yl, imidazo[2,1-b][1,3]thiazoi-2-yl, imidazo[2,1-b][1,3]thiazol-3-yl, imidazo[2,1-b][1,3]thiazol-5-yl or imidazo[2,1-b][1,3]thiazol-6-yl, imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl or imidazo[1,2-a]pyridin-7-yl, tetrazolo[1,5-a]pyridine-5-yl, tetrazolo[1,5-a]pyridine-6-yl, tetrazolo[1,5-a]pyridine-7-yl, or tetrazolo[1,5-a]pyridine-8-yl, 2-, 6-, 7- or 8-purinyl, 4-, 5- or 6-phthalazinyl, 2-, 3- or 4-naphthyridinyl, 2-, 5- or 6-quinoxalinyl, 2-, 4-, 5-, 6-, 7- or 8-quinazolinyl, 1-, 2-, 3- or 4-quinolizinyl, 2-, 3-, 4-, 5-, 6-, 7-, or 8-quinolinyl(quinolyl), 2-, 4-, 5-, 6-, 7- or 8-quinazolyl, 1-, 3-, 4-, 5-, 6-, 7- or 8-isoquinolinyl(isoquinolyl), 3-, 4-, 5-, 6-, 7- or 8-cinnolinyl, 2-, 4-, 6- or 7-pteridinyl, 1-, 2-, 3-, 4- or 9-carbazolyl, 1-, 2-, 3-, 4-, 5-, 6-, 7-, 8- or 9-carbolinyl, 1-, 2-, 3-, 4-, 5-, 6-, 7-, 8-, 9- or 10-phenanthridinyl, 1-, 2-, 3- or 4-acridinyl, 1-, 2-, 3-, 4-, 5-, 6-, 7-, 8- or 9-perimidinyl, 2-, 3-, 4-, 5-, 6-, 7-, 8-, 9- or 10-(1,7)phenanthrolinyl, 1- or 2-phenazinyl, 1-, 2-, 3-, 4-, or 10-phenothiazinyl, 3- or 4-furazanyl, 1-, 2-, 3-, 4-, or 10-phenoxazinyl, or additionally substituted derivatives thereof.

An "optionally substituted heteroaryl" refers to a heteroaryl having optionally one or more substituents (for example 1 to 4 substituents, for example 1, 2, 3 or 4), selected from those defined above for substituted aryl.

The term "oxo" as used herein refers to the group =O.

The term "alkoxy" or "alkyloxy" as used herein refers to a radical having the Formula —OR$^b$ wherein R$^b$ is alkyl. Preferably, alkoxy is $C_1$-$C_{10}$ alkoxy, $C_1$-$C_6$ alkoxy, or $C_1$-$C_4$ alkoxy. Non-limiting examples of suitable alkoxy include methoxy, ethoxy, propoxy, isopropoxy, butoxy, isobutoxy, sec-butoxy, tert-butoxy, pentyloxy and hexyloxy. Where the oxygen atom in an alkoxy group is substituted with sulfur, the resultant radical is referred to as thioalkoxy. "Haloalkoxy" is an alkoxy group wherein one or more hydrogen atoms in the alkyl group are substituted with halogen. Non-limiting examples of suitable haloalkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy; trichloromethoxy, 2-bromoethoxy, pentafluoroethyl, 3,3,3-trichloropropoxy, 4,4,4-trichlorobutoxy.

The term "aryloxy" as used herein denotes a group —O-aryl, wherein aryl is as defined above.

The term "arylcarbonyl" or "aroyl" as used herein denotes a group —C(O)-aryl, wherein aryl is as defined above.

The term "cycloalkylalkyl" by itself or as part of another substituent refers to a group having one of the aforementioned cycloalkyl groups attached to one of the aforementioned alkyl chains. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, 3-cyclopentylbutyl, cyclohexylbutyl and the like.

The term "heterocyclyl-alkyl" by itself or as part of another substituents refers to a group having one of the aforementioned heterocyclyl group attached to one of the aforementioned alkyl group, i.e., to a group —R$^d$—R$^b$ wherein R$^d$ is alkylene or alkylene substituted by alkyl group and R$^b$ is a heterocyclyl group.

The term "carboxy" or "carboxyl" or "hydroxycarbonyl" by itself or as part of another substituent refers to the group —CO$_2$H. Thus, a carboxyalkyl is an alkyl group as defined above having at least one substituent that is —CO$_2$H.

The term "alkoxycarbonyl" by itself or as part of another substituent refers to a carboxy group linked to an alkyl radical i.e. to form —C(=O)OR$^e$, wherein R$^e$ is as defined above for alkyl.

The term "alkylcarbonyloxy" by itself or as part of another substituent refers to a —O—C(=O)R$^e$ wherein R$^e$ is as defined above for alkyl.

The term "alkylcarbonylamino" by itself or as part of another substituent refers to an group of Formula —NH(C=O)R or —NR'(C=O)R, wherein R and R' are each independently alkyl or substituted alkyl.

The term "thiocarbonyl" by itself or as part of another substituent refers to the group —C(=S)—.

The term "alkoxy" by itself or as part of another substituent refers to a group consisting of an oxygen atom attached to one optionally substituted straight or branched alkyl group, cycloalkyl group, aralkyl, or cycloalkylalkyl group. Non-limiting examples of suitable alkoxy group include methoxy, ethoxy, n-propoxy, isopropoxy, n-butoxy, iso-butoxy, sec-butoxy, tert-butoxy, hexanoxy, and the like.

The term "halo" or "halogen" as a group or part of a group is generic for fluoro, chloro, bromo, or iodo.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl, and the like.

The term "haloaryl" alone or in combination, refers to an aryl radical having the meaning as defined above wherein one or more hydrogens are replaced with a halogen as defined above.

The term "haloalkoxy" alone or in combination refers to a group of Formula —O-alkyl wherein the alkyl group is substituted by 1, 2, or 3 halogen atoms. For example, "haloalkoxy" includes —OCF$_3$, —OCHF$_2$, —OCH$_2$F, —O—CF$_2$—CF$_3$, —O—CH$_2$—CF$_3$, —O—CH$_2$—CHF$_2$, and —O—CH$_2$—CH$_2$F.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

As described herein, some of the compounds of the invention may contain one or more asymmetric carbon atoms that serve as a chiral center, which may lead to different optical forms (e.g. enantiomers or diastereoisomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I and any subgroup thereof. This term also refers to compounds as depicted in tables hereinbelow, their derivatives, N-oxides, salts, solvates, hydrates, stereoisomeric forms, racemic mixtures, tautomeric forms, optical isomers, analogues and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

As used herein, the term "ROCK" refers to either of the ROCK-I or ROCK-II isoforms or both. The terms "ROCK-I", "ROCK1" or any of their synonyms accepted in the art encompasses the known naturally occurring or biologically engineered mutants and constructs of ROCK-I. The terms "ROCK-2", "ROCK2" or any of their synonyms accepted in the art encompasses the known naturally occurring or biologically engineered mutants and constructs of ROCK-II.

Whenever used in the present document, the terms "soft inhibitor(s)", "soft kinase inhibitors", "soft ROCK inhibitors" or similar terms refer to compounds possessing inhibitory properties against ROCK, which are stable in a target organ, but are rapidly converted into a predictable, functionally inactive species once entering the systemic circulation. This inactivation process can occur in liver, but is preferentially achieved in blood.

As used herein, the term "target organ" refers to an organ (eg: eye), organ part (eg cornea, retina) or cellular tissue where inhibition of ROCK is expected to result in beneficial effects.

As used herein, the terms "functionally active species" of "functionally active compound" refer to a compound displaying significant in vivo activity and/or significant activity in cellular assays that are acknowledged in the art as physiologically relevant readouts of cellular ROCK activity. An example of such cellular assays is a Myosin Light Chain phosphorylation assay described by Schröter et al in *Biochemical and Biophysical Research Communications* 374 (2008) 356-360, which has been used to evaluate the cellular activity of compounds of the present invention (see Examples, section C.1.2). As used herein, the terms "functionally inactive species" or "functionally inactive compound" refer to a compound displaying markedly reduced, preferably negligible activity in the same in vivo or cellular readouts of ROCK activity.

As used herein, the terms "esterase" or "esterases" encompasses all enzymes displaying carboxylic ester hydrolase (EC 3.1.1) activity. This definition includes enzymes displaying additional hydrolytic activity on substrates that are not carboxylic esters. For example; Paraoxonase 1 (PON1) displays aryldialkylphosphatase activity (EC 3.1.8.1, also known as paraoxonase activity, hence its name) and diisopropyl-fluorophosphatase activity (EC 3.1.8.2), but also arylesterase activity (EC 3.1.1.2) and lactonase activity. PON1 is therefore considered as an esterase. As used herein, the term "pseudoesterase" refers to a protein displaying some degree of carboxylic ester hydrolase activity, but low catalytic efficiency against carboxylic esters. Some proteins known as pseudoesterases, such as serum albumin, actually lack a true catalytic site.

In a further embodiment, the present invention provides compounds of formula I

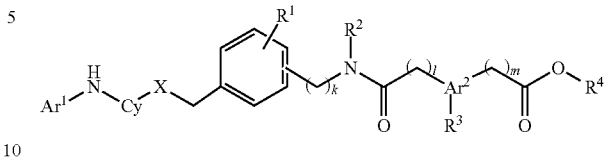

Wherein
$Ar^1$ is selected from the group comprising

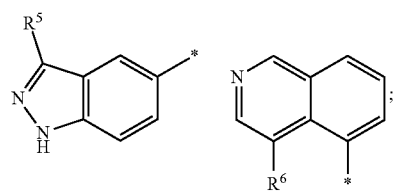

$Ar^2$ represents an aryl or heteroaryl;
Cy is a $C_{3-15}$cycloalkyl wherein optionally one carbon atom is replaced by a nitrogen atom;
X is a direct bond, —NH— or —NC$_{1-6}$alkyl-;
$R^1$ is selected from the group comprising hydrogen, halogen, $C_{1-6}$ alkyl, and $C_{1-6}$ alkoxyl;
$R^2$ is selected from the group comprising hydrogen and $C_{1-3}$ alkyl;
$R^3$ is selected from the group comprising hydrogen, halogen, $C_{1-6}$ alkyl, and $C_{1-6}$ alkoxyl;
$R^4$ is an optionally substituted group selected from the group comprising $C_{1-20}$alkyl, $C_{1-20}$alkenyl, $C_{1-20}$alkynyl, $C_{3-15}$cycloalkyl, aryl, heterocyclyl, and heteroaryl;
$R^5$ is selected from hydrogen, $C_{1-6}$alkyl and $NH_2$;
$R^6$ is selected from hydrogen, halo or $C_{1-6}$alkyl; in particular selected from hydrogen, halo or methyl;
k is an integer from 0 to 3;
l is an integer from 0 to 3;
m is an integer from 0 to 3;
with the proviso that when Cy contains a nitrogen atom, then X is a direct bond; and when Cy does not contain a nitrogen atom, then X is —N(C$_{1-6}$alkyl)- or —NH—.

In a further particular embodiment, Cy is $C_{3-10}$cycloalkyl wherein optionally one carbon atom is replaced by a nitrogen atom. In another particular embodiment, Cy is $C_{3-10}$cycloalkyl wherein one carbon atom is replaced by a nitrogen atom.

In another particular embodiment, the present invention provides compounds of formula I as described herein, with the proviso that when X is a direct bond and Cy is an N-containing heterocyclic group, then Cy is connected through a nitrogen atom in its ring(s) to

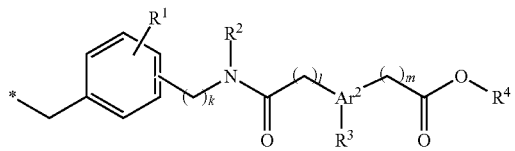

In particular, Cy is connected through a nitrogen atom in its ring(s) to

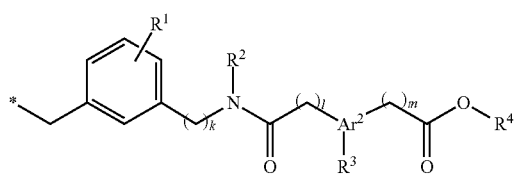

In yet another embodiment, the present invention provides compounds of formula I, wherein -Cy-X— is selected from the group consisting of:

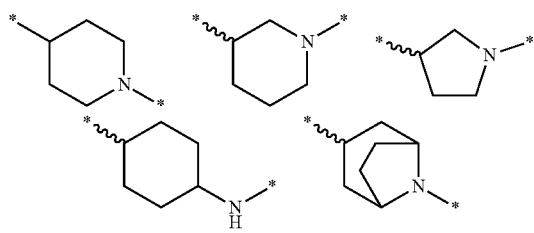

in particular from the group consisting of:

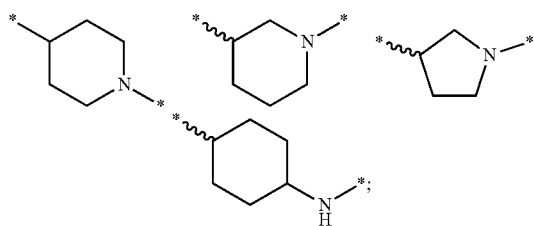

more in particular from the group consisting of:

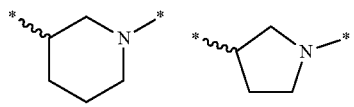

In a further embodiment, the present invention provides compounds of formula I, wherein
$Ar^2$ is aryl; in particular phenyl.

In yet another embodiment, the present invention provides compounds of formula I, wherein $R^1$ is selected from the group consisting of hydrogen, halogen, methyl, and methoxyl; in particular hydrogen, fluoro, chloro, methyl, and methoxyl.

In a further embodiment, the present invention provides compounds of formula I, wherein $R^1$ is selected from the group consisting of hydrogen, halogen, and $C_{1-6}$alkyl; in particular hydrogen, fluoro, chloro, and methyl.

In a particular embodiment, the present invention provides compounds of formula I, wherein $R^2$ is hydrogen.

In another particular embodiment, the present invention provides compounds of formula I, wherein $R^3$ is hydrogen or $C_{1-6}$alkoxyl; in particular hydrogen or $C_{1-2}$alkoxyl.

In a further embodiment, the present invention provides compounds of formula I, wherein $R^3$ is hydrogen or halogen; in particular hydrogen, chloro, or fluoro; more in particular hydrogen.

In yet another particular embodiment, the present invention provides compounds of formula I, wherein $R^4$ is an optionally substituted group selected from the group consisting of $C_{1-20}$alkyl; $C_{3-15}$cycloalkyl, and heterocyclyl; in particular from the group consisting of $C_{1-20}$alkyl; $C_{3-10}$cycloalkyl, and heterocyclyl; more in particular $R^4$ is optionally substituted $C_{1-20}$alkyl.

In another particular embodiment, $R^4$ is an optionally substituted group selected from the group consisting of $C_{1-20}$alkyl, $C_{3-15}$cycloalkyl, aryl, heteroaryl, and heterocyclyl; in particular $R^4$ is an optionally substituted group selected from the group consisting of $C_{1-20}$alkyl, $C_{3-15}$cycloalkyl, aryl, and heterocyclyl.

In a further embodiment, the optional substituents within the $R^4$ definition are selected from halo, hydroxyl, nitro, amino, cyano, aryl, cycloalkyl, heterocyclyl, alkyl, alkenyl, alkynyl, alkylamino, dialkylamino, and alkoxy; in particular $C_{1-6}$alkoxy, $C_{1-6}$alkyl, $C_{1-6}$alkenyl, $C_{1-6}$alkynyl, dialkylamino, and heterocyclyl; more in particular methyl, methoxyl, ethynyl, dimethylamino and oxolanyl.

In another further embodiment, the optional substituents within the $R^4$ definition are selected from $C_{1-6}$alkoxy and heterocyclyl; in particular methoxyl and oxolanyl.

In another embodiment, the present invention provides compounds of formula I, wherein $R^5$ is selected from the group consisting of hydrogen, methyl, and $NH_2$; in particular $R^5$ is hydrogen.

In yet another embodiment, the present invention provides compounds of formula I, wherein $R^6$ is hydrogen, fluoro, or methyl; in particular hydrogen.

In a further embodiment, the present invention provides compounds of formula I, wherein k is 0 or 1; in particular 0.

In another further embodiment, the present invention provides compounds of formula I, wherein l is 0 or 1; in particular 0.

In yet another further embodiment, the present invention provides compounds of formula I, wherein m is 0 or 1.

It is also an object of the present invention to provide those compounds of formula I as described herein, wherein one or more of the following restrictions apply:
$Ar^1$ is

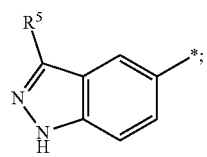

$Ar^1$ is

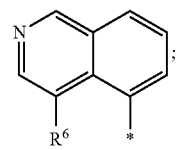

$Ar^2$ is aryl, in particular phenyl;
Cy is a $C_{3-15}$cycloalkyl wherein optionally one carbon atom is replaced by a nitrogen atom;
Cy is a $C_{3-15}$cycloalkyl wherein one carbon atom is replaced by a nitrogen atom;
when X is a direct bond, Cy is connected through a nitrogen atom in its ring(s) to

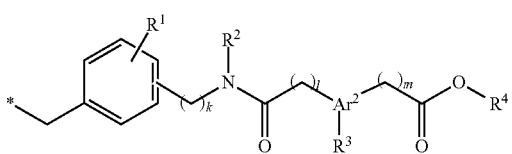

In particular, Cy is connected through a nitrogen atom in its ring(s) to

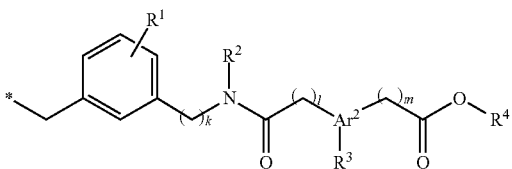

when Cy contains a nitrogen atom, then X is a direct bond; and when Cy does not contain a nitrogen atom, then X is —N($C_{1-6}$alkyl)- or —NH—;

-Cy-X— is selected from the group consisting of

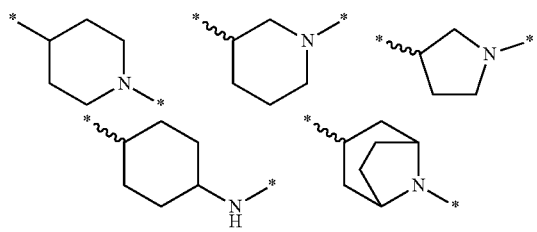

in particular from the group consisting of:

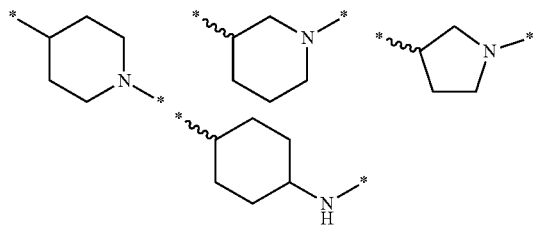

more in particular from the group consisting of:

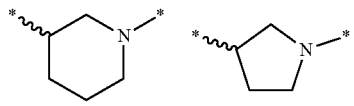

$R^1$ is selected from the group consisting of hydrogen, halogen, methyl, and methoxyl; in particular hydrogen, fluoro, chloro, methyl, and methoxyl.

$R^1$ is selected from the group consisting of hydrogen, halogen, and $C_{1-6}$alkyl; in particular hydrogen, fluoro, chloro, and methyl.

$R^2$ is hydrogen;

$R^3$ is hydrogen or $C_{1-6}$alkoxyl; in particular hydrogen or $C_{1-2}$alkoxyl; more in particular hydrogen or ethoxyl.

$R^3$ is hydrogen or halogen; in particular hydrogen, chloro, or fluoro; more in particular hydrogen.

$R^4$ is an optionally substituted group selected from the group consisting of $C_{1-20}$alkyl; $C_{3-15}$cycloalkyl, and heterocyclyl; in particular $R^4$ is optionally substituted $C_{1-20}$alkyl.

$R^4$ is an optionally substituted group selected from the group consisting of $C_{1-20}$alkyl, $C_{3-15}$cycloalkyl, aryl, heteroaryl, and heterocyclyl; in particular $R^4$ is an optionally substituted group selected from the group consisting of $C_{1-20}$alkyl, $C_{3-15}$cycloalkyl, aryl, and heterocyclyl.

the optional substituents within the $R^4$ definition are selected from $C_{1-6}$alkoxy and heterocyclyl; in particular methoxyl and oxolanyl.

the optional substituents within the $R^4$ definition are selected from halo, hydroxyl, nitro, amino, cyano, aryl, cycloalkyl, heterocyclyl, alkyl, alkenyl, alkynyl, alkylamino, dialkylamino, and alkoxy; in particular $C_{1-6}$alkoxy, $C_{1-6}$alkyl, $C_{1-6}$alkenyl, $C_{1-6}$alkynyl, dialkylamino, and heterocyclyl; more in particular methyl, methoxyl, ethynyl, dimethylamino and oxolanyl.

$R^5$ is selected from the group consisting of hydrogen, methyl, and $NH_2$; in particular $R^5$ is hydrogen.

$R^6$ is hydrogen, fluoro, or methyl; in particular hydrogen;

k is 0 or 1; in particular 0;

l is 0 or 1; in particular 0;

m is 0 or 1.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

In a preferred embodiment, the compounds of the present invention are useful as kinase inhibitors, more in particular for the inhibition of at least one ROCK kinase, selected from ROCKI and ROCKII, in particular soft ROCK inhibitors.

The present invention further provides the use of a compound as defined hereinbefore or the use of a composition comprising said compound, as a human or veterinary medicine, in particular for prevention and/or treatment of at least one disease or disorder, in which ROCK is involved, such as diseases linked to smooth muscle cell function, inflammation, fibrosis, excessive cell proliferation, excessive angiogenesis, hyperreactivity, barrier dysfunction, neurodegeneration, and remodeling.

In a further embodiment, the invention provides the use of a compound as defined hereinbefore, or the use of a composition comprising said compound in the prevention and/or treatment of at least one disease or disorder selected from the group comprising eye diseases; airway diseases; throat, nose and ear diseases; intestinal diseases; cardiovascular and vascular diseases; inflammatory diseases; neurological and CNS disorders: proliferative diseases; kidney diseases; sexual dysfunction; bone diseases; benign prostatic hyperplasia, transplant rejection, spasm, hypertension, chronic obstructive bladder disease, and allergy.

In a preferred embodiment, the invention provides the use of a compound as defined hereinbefore or the use of a composition comprising said compound in the prevention and/or treatment of eyes diseases and disorders including but not limited to retinopathy, optic neuropathy, glaucoma and degenerative retinal diseases such as age-related macular degeneration, retinitis pigmentosa and inflammatory eye diseases, and/or for preventing, treating and/or alleviating complications and/or symptoms associated therewith.

In another preferred embodiment, the invention provides the use of a compound as defined hereinbefore or the use of a composition comprising said compound in the prevention and/or treatment of airway diseases; including but not limited to pulmonary fibrosis, emphysema, chronic bronchitis, asthma, fibrosis, pneumonia, cystic fibrosis, chronic obstructive pulmonary disease (COPD); bronchitis and rhinitis and respiratory distress syndrome, and/or for preventing, treating and/or alleviating complications and/or symptoms associated therewith.

In a further embodiment, the invention provides the use of a compound as defined hereinbefore or the use of a composition comprising said compound in the prevention and/or treatment of cardiovascular and vascular diseases: including but not limited to pulmonary hypertension and pulmonary vasoconstriction, and/or for preventing, treating and/or alleviating complications and/or symptoms associated therewith and/or alleviating complications and/or symptoms associated therewith.

In a further embodiment, the invention provides the use of a compound as defined hereinbefore or the use of a composition comprising said compound in the prevention and/or treatment of Throat, Nose and Ear diseases: including but not limited to sinus problems, hearing problems, toothache, tonsillitis, ulcer and rhinitis, In a further embodiment, the invention provides the use of a compound as defined hereinbefore or the use of a composition comprising said compound in the prevention and/or treatment of skin diseases: including but not limited to hyperkeratosis, parakeratosis, hypergranulosis, acanthosis, dyskeratosis, spongiosis and ulceration.

In a further embodiment, the invention provides the use of a compound as defined hereinbefore or the use of a composition comprising said compound in the prevention and/or treatment of Intestinal diseases; including but not limited to inflammatory bowel disease (IBD), colitis, gastroenteritis, ileus, ileitis, appendicitis and Crohn's disease.

In yet another embodiment, the invention provides the use of a compound as defined hereinbefore or the use of a composition comprising said compound in the prevention and/or treatment of inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis, and/or for preventing, treating and/or alleviating complications and/or symptoms and/or inflammatory responses associated therewith.

In another embodiment, the invention provides the use of a compound as defined hereinbefore or the use of a composition comprising said compound in the prevention, treatment and/or management of neurological and CNS disorders: including but not limited to neuropathic pain. The present compounds are therefore suitable for preventing neurodegeneration and stimulating neurogeneration in various neurological disorders, and/or for preventing, treating and/or alleviating complications and/or symptoms associated therewith.

In another embodiment, the invention provides the use of a compound as defined hereinbefore or the use of a composition comprising said compound in the prevention and/or treatment of proliferative diseases: such as but not limited to cancer of breast, colon, intestine, skin, head and neck, nerve, uterus, kidney, lung, ovary, pancreas, prostate, or thyroid gland; Castleman disease; sarcoma; malignoma; and melanoma; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of kidney diseases: including but not limited to renal fibrosis or renal dysfunction; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of sexual dysfunction: including but not limited to hypogonadism, bladder disease, hypertension, diabetes, or pelvic surgery; and/or to treat sexual dysfunction associated with treatment using certain drugs, such as drugs used to treat hypertension, depression or anxiety.

In another embodiment, the invention provides the use of a compound as defined hereinbefore or the use of a composition comprising said compound in the prevention and/or treatment of bone diseases: including but not limited to osteoporosis and osteoarthritis; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of diseases and disorders such as benign prostatic hyperplasia, transplant rejection, spasm, chronic obstructive bladder disease, and allergy, and/or for preventing, treating and/or alleviating complications and/or symptoms associated therewith.

In a preferred embodiment the present invention provides the use of a compound as defined hereinbefore or the use of a composition comprising said compound in the prevention and/or treatment of glaucoma, macular degeneration (including age-related macular degeneration), asthma, sexual dysfunction or COPD.

Method of Treatment

The present invention further provides a method for the prevention and/or treatment of at least one disease or disorder in which ROCK is involved; said method comprising administering to a subject in need thereof a therapeutic effective amount of a compound or composition of the invention.

In a further embodiment, the present invention further provides a method for the prevention and/or treatment of at least one disease or disorder selected from the group comprising eye diseases; airway diseases; throat, nose and ear diseases; intestinal diseases; cardiovascular and vascular diseases; inflammatory diseases; neurological and CNS disorders: proliferative diseases; kidney diseases; sexual dysfunction; bone diseases; benign prostatic hyperplasia; transplant rejection; spasm; hypertension; chronic obstructive bladder disease and allergy; said method comprising administering to a subject in need thereof a therapeutic effective amount of a compound or a composition of the invention.

In the invention, particular preference is given to compounds of Formula I or any subgroup thereof that in the inhibition assay for ROCK described below inhibit ROCK with an $IC_{50}$ value of less than 10 µM, preferably less than 1 µM, more preferably less than 0.1 µM.

Said inhibition may be effected in vitro and/or in vivo, and when effected in vivo, is preferably effected in a selective manner, as defined above.

The term "ROCK-mediated condition" or "disease", as used herein, means any disease or other deleterious condition in which is known to play a role. The term "ROCK-mediated condition" or "disease" also means those diseases or conditions that are alleviated by treatment with a ROCK inhibitor.

Accordingly, another embodiment of the present invention relates to treating or lessening the severity of one or more diseases in which ROCK is known to play a role.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person.

The pharmaceutically acceptable salts of the compounds according to the invention, i.e. in the form of water-, oil-soluble, or dispersible products, include the conventional non-toxic salts which are formed, e.g., from inorganic or organic acids. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intramuscular or subcutaneous injection, for intravitreal injection, for topical administration (including ocular), for administration by inhalation, by a skin patch, by an implant, by a suppository, etc. . . . . Such suitable administration forms—which may be solid, semi-solid or liquid, depending on the manner of administration—as well as methods and carriers, diluents and excipients for use in the preparation thereof, will be clear to the skilled person.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is made to standard handbooks, such as the latest edition of Remington's Pharmaceutical Sciences.

The compounds can be administered by a variety of routes including the oral, rectal, ocular, transdermal, or intranasal routes, depending mainly on the specific preparation used and the condition to be treated or prevented, (e.g. eye drops for the treatment of eye diseases or dry powder inhaler for the treatment of lung diseases). The at least one compound of the invention will generally be administered in an "effective amount", by which is meant any amount of a compound of the Formula I or any subgroup thereof that, upon suitable administration, is sufficient to achieve the desired therapeutic or prophylactic effect in the individual to which it is administered. The amount(s) to be administered, the route of administration and the further treatment regimen may be determined by the treating clinician, depending on factors such as the age, gender and general condition of the patient and the nature and severity of the disease/symptoms to be treated.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

In preferred embodiments, the compounds and compositions of the invention are used locally, for instance topical or in both absorbed and non-adsorbed applications.

The compositions are of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a composition for veterinary use that contains at least one compound of the invention and at least one suitable carrier (i.e. a carrier suitable for veterinary use). The invention also relates to the use of a compound of the invention in the preparation of such a composition. Thus, the present invention provides the use of a compound of the invention in the preparation of a medicament for the treatment of a disease or disorder in which ROCK is involved.

The invention will now be illustrated by means of the following synthetic and biological examples, which do not limit the scope of the invention in any way.

EXAMPLES

A. Physicochemical Properties of the Compounds

A.1. Compound Purity

Unless indicated otherwise, the purity of the compounds was confirmed as follows:
Liquid chromatography/mass spectrometry (LC/MS, HPLC/MS or UPLC/MS), C18 column.
$^1$H NMR

A.2. Stereochemistry

It is known by those skilled in the art that specific enantiomers (or diastereoisomers) can be obtained by different methods such as, but not limited to chiral resolution (for example, salts formed with optically active acids or bases may be used to form diastereoisomeric salts that can facilitate the separation of optically active isomers of the compounds of Formula I or any subgroup thereof), assymetric synthesis or preparative chiral chromatography (using different column such as Chiralcel OD-H (tris-3,5-dimethylphenylcarbamate, 46×250 or 100×250 mm, 5 μm), Chiralcel OJ (tris-methylbenzoate, 46×250 or 100×250 mm, 5 μm), Chiralpak AD (tris-3,5-dimethylphenylcarbamate, 46×250 mm, 10 μm) and Chiralpak AS (tris-(S)-1-phenylethylcarbamate, 46×250 mm, 10 μm) from Chiral Technologies Europe (Illkirch, France)). Whenever it is convenient, stereoisomers can be obtained starting from commercial materials with known configuration (such compounds include aminoacids for instance).

When necessary, the Cahn-Ingold-Prelog system was used to attribute the absolute configuration of chiral center, in which the four groups on an asymmetric carbon are ranked to a set of sequences rules. Reference is made to Cahn; Ingold; Prelog Angew. Chem. Int. Ed. Engl. 1966, 5, 385-415.

B. Compound Synthesis

B.1. Intermediates

The compounds of the invention may be prepared by methods well known to those skilled in the art, and as described in the synthetic and experimental procedures shown below.

Intermediate 1:
Isoquinolin-5-yl-piperidin-3-yl-amine hydrochloric acid salt

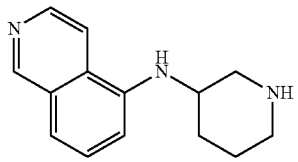 [SMILES: c1cc(NC2CCCNC2)c2ccncc2c1]

To a solution of isoquinoline (120 g, 0.929 mol) in $H_2SO_4$ (1 L) was added $KNO_3$ (112.6 g, 1.115 mol) at −15° C. (dropwise). The mixture was stirred at room temperature for 2 hours. TLC (petroleum ether:ethyl acetate=2:1) showed complete conversion. The mixture was added to water (3 L) at 0° C. The mixture was adjusted to pH 8 by the addition of $NH_4OH$ and filtered. The filter cake was washed with methyl tertbutyl ether (1 L×2) and concentrated under vacuum to give 5-nitro-isoquinoline (160 g, 94%) as a yellow solid.

To a solution of 5-nitro-isoquinoline (150 g, 0.861 mol) in $EtOH/H_2O=4:1$ (5 L) was added $NH_4Cl$ (92.2 g, 1.723 mol) and Fe (193 g, 3.445 mol) at room temperature. Then the mixture was heated to 80° C. and stirred for 10 hours. TLC (petroleum ether:ethyl acetate=1:1) showed complete conversion. The mixture was cooled to room temperature and filtered through a pad of celite. The filter cake was washed with EtOH (2 L×2) and the filtrate concentrated under vacuum. The residue was extracted with EtOAc (500 mL×10) and the combined layers dried over $Na_2SO_4$, filtered and then concentrated under vacuum to afford 5-amino-isoquinoline (67 g, 54%) as a yellow solid.

To a solution of 5-amino-isoquinoline (47 g, 0.320 mol) in $CH_3COOH$ (1800 mL) was added 3-amino-piperidine-1-carboxylic acid tert-butyl ester (69.6 g, 0.376 mol) and $Na_2SO_4$ (267 g, 1.88 mol) at room temperature. The mixture was stirred at room temperature for 0.5 hour. Then to the mixture was added $NaBH(OAc)_3$ (84.6 g, 0.376 mol) by portions. The mixture was stirred at room temperature for 18 hours. The mixture was adjusted to pH 8 by the addition of $K_2CO_3$ and extracted with EtOAc (2 L×3). The combined layers were dried over $Na_2SO_4$, filtered and then concentrated under vacuum. The residue was purified by column chromatography on silica gel (petroleum ether:ethyl acetate=5:1) to give 3-(isoquinolin-5-ylamino)-piperidine-1-carboxylic acid tert-butyl ester (55 g, 53%) as a yellow oil.

To a solution of 3-(isoquinolin-5-ylamino)-piperidine-1-carboxylic acid tert-butyl ester (80 g, 0.244 mol) in EtOAc (1000 mL) was added HCl-EtOAc (1000 mL) at room temperature. The mixture was stirred at room temperature for 2.5 hours. TLC (DCM:MeOH=10:1) showed complete conversion. The solid was collected by filtration and dried under vacuum to give the title compound (66 g, 100%) as a yellow solid.

Intermediate 2:
N-(pyrrolidin-3-yl)isoquinolin-5-amine

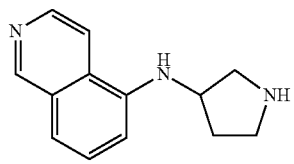 [SMILES: c1cc(NC2CCNC2)c2ccncc2c1]

To a homogenous solution of isoquinolin-5-amine (15 g, 104 mmol) and tert-butyl 3-oxopyrrolidine-1-carboxylate (23.12 g, 125 mmol, 1.2 eq) in AcOH (300 mL) at 0° C. was added dropwise a solution of $NaBH(OAc)_3$ (44.1 g, 208 mmol, 2 eq) in AcOH (200 mL). The mixture was stirred at room temperature overnight and concentrated to dryness. Then, the residue was adjusted to pH 10 by addition of saturated aqueous solution of $Na_2CO_3$ and extracted with DCM (×3). The combined organic layers were dried over $Na_2SO_4$, filtered and then concentrated under vacuum to afford the expected compound, which was used directly in the next step without further purification.

To a solution of previous compound (104 mmol) in diethylether (1 L) was bubbled HCl gas for 1 hour. The suspension was stirred for 5 h and the solvent evaporated. Then, the residue was dissolved in water and the pH adjusted to pH>12 by addition of NaOH 5 M. The aqueous layer was extracted with DCM (×3) and the combined organic layers, dried over $Na_2SO_4$, filtered and concentrated under vacuum to give the intermediate 2 (20.5 g, 92%) as a brown powder.

Intermediate 3:
5-(Piperidin-3-ylamino)-indazole-1-carboxylic acid tert-butyl ester

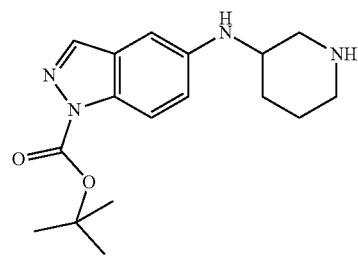 [SMILES: CC(C)(C)OC(=O)n1ncc2cc(NC3CCCNC3)ccc21]

To a solution of 5-nitro-indazole (200 g, 1.2 mol, 1.0 eq) in THF (2 L) were added DMAP (22 g, 0.18 mol, 0.15 eq) and TEA (248 g, 2.4 mol, 2.0 eq). The reaction mixture was stirred at 30° C. for 20 min, then $Boc_2O$ (320 g, 1.5 mol, 1.2 eq) was added to the reaction mixture in one portion. The reaction mixture was stirred at 30° C. for 16 hours, concentrated and the residue was dissolved in DCM (2 L). The DCM solution was washed with aq HCl (0.5M) (1 L×3) and $H_2O$ (1 L×3), dried over $MgSO_4$ and concentrated to dryness to give the Boc protected 5-nitro-indazole (310 g, 96%).

To a solution of 5-nitro-indazole-1-carboxylic acid tert-butyl ester (300 g, 1.1 mol, 1.0 eq) in THF (3 L) was added Pd/C (30 g). The reaction mixture was stirred at 40° C. for 16 hours under pressure of $H_2$ (50 psi). TLC (PE:EtOAc=4:1) showed complete conversion. After uptake of $H_2$, the catalyst was filtered off and the filtrate was evaporated to afford the crude 5-amino-indazole-1-carboxylic acid tert-butyl ester (252 g, 95%) which was used directly for next step without purification.

A mixture of 1-benzyl-piperidin-3-one hydrochloride (116 g, 0.52 mol, 1.2 eq) and TEA (43.5 g, 0.43 mol, 1.0 eq) in DCE (800 mL) was stirred at 30° C. for 1 hour. Then 5-amino-indazole-1-carboxylic acid tert-butyl ester (100 g, 0.43 mol, 1.0 eq) and $CH_3COOH$ (25.8 g, 0.43 mol, 1.0 eq) were added and the reaction mixture stirred for 30 min. $NaBH(OAc)_3$ (273 g, 1.29 mol, 3.0 eq) was then added in one portion and the mixture stirred at 30° C. for 16 hours. LC-MS showed complete conversion. The reaction mixture was diluted in DCM (1 L) and the organic layer washed with saturated $NaHCO_3$ (800 mL×3) and $H_2O$ (500 mL×3), dried over $Na_2SO_4$ and concentrated under vacuum. The crude product was purified by column chromatography on silica gel using (DCM:MeOH=60:1) to give the 5-(1-benzyl-piperidin-3-ylamino)-indazole-1-carboxylic acid tert-butyl ester (131 g, 75%).

To a solution of the previous compound (120 g, 0.3 mol, 1.0 eq) in $CH_3OH$ (1.5 L) was added Pd/C (12 g) and the reaction mixture stirred at 40° C. under pressure of $H_2$ (50 psi) for 16 hours. TLC (DCM:MeOH=10:1) showed complete conversion. After uptake of $H_2$, the catalyst was filtered off and the filtrate was evaporated to afford the intermediate 3 (90 g, 95%) which was used directly for next step without purification.

Intermediate 4: N-(1-(3-nitrobenzyl)pyrrolidin-3-yl)isoquinolin-5-amine

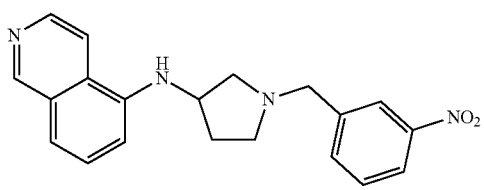 [SMILES: O=[N+]([O-])c1cccc(CN2CCC(Nc3cccc4cnccc34)C2)c1]

A mixture of intermediate 2 (8.3 g, 39 mmol) and 3-nitrobenzaldehyde (5.9 g, 39 mmol) in MeOH (100 mL) was stirred at rt for 30 min. Then $NaBH(OAc)_3$ (16.3 g, 78 mmol) was added by portions and the mixture stirred at rt overnight. Then MeOH was removed by evaporation under vacuum, the residue dissolved in water and extracted with EtOAc (100 mL×3). The combined organic layers were washed with sat. $NaHCO_3$, dried over $MgSO_4$, filtered and concentrated under vacuum. The residue was purified by column chromatography to give the intermediate 4 (7 g, 51%).

Intermediate 5: 1-N-(isoquinolin-5-yl)-4-N-(3-nitrobenzyl)cyclohexane-1,4-diamine

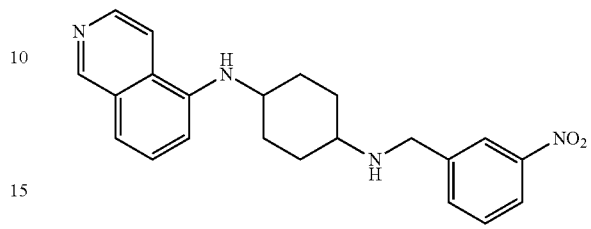

To a solution of tert-butyl N-(4-aminocyclohexyl)carbamate (25 g, 117 mmol, 1.0 eq) and 3-nitrobenzaldehyde (18 g, 117 mmol, 1.0 eq) in MeOH (500 mL) was added $NaBH(OAc)_3$ (50 g, 234 mmol, 2.0 eq) by portions. Then the resulting mixture was stirred overnight at 30° C. LC-MS indicated complete conversion. The solvent was removed under vacuum and the residue was purified by column chromatography (DCM:MeOH=15:1) to provide tert-butyl N-(4-[(3-nitrobenzyl)amino]cyclohexyl)carbamate (33 g, 83%) as a yellow solid.

Tert-butyl N-(4-[(3-nitrobenzyl)amino]cyclohexyl)carbamate (30.0 g, 86.1 mmol, 1.0 eq) was dissolved in 300 mL of TFA:DCM (1:10) and the resulting solution was stirred at 30° C. overnight. The reaction mixture was then concentrated under vacuum to provide crude 1-N-(3-nitrobenzyl)cyclohexane-1,4-diamine (32 g, TFA salt) as a white solid.

To a solution of 1-N-(3-nitrobenzyl)cyclohexane-1,4-diamine TFA salt (32 g, 69.6 mmol, 1.2 eq) in toluene (500 mL) were added 5-bromoisoquinoline (12 g, 58.0 mmol, 1.0 eq), BINAP (3.6 g, 5.8 mmol, 0.1 eq), NaOtBu (33 g, 347.8 mmol, 6.0 eq) and $Pd_2(dba)_3$ (5.3 g, 5.8 mmol, 0.1 eq). The reaction mixture was submitted to 3 vaccum-$N_2$ cycles and then stirred at 80° C. overnight. LC-MS indicated complete conversion. Toluene was removed under reduced pressure and the residue was purified by column chromatography (DCM:MeOH=15:1) to provide intermediate 5 (15 g, 71%) as a yellow solid.

Intermediate 6: N-{1-(3-nitrobenzyl)piperidin-4-yl}isoquinolin-5-amine

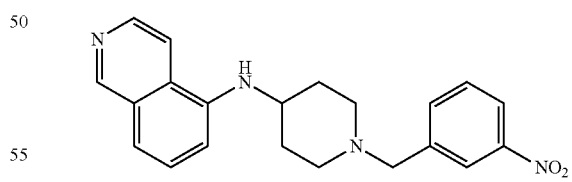

To a mixture of tert-butyl N-(piperidin-4-yl)carbamate (25 g, 125 mmol, 1.0 eq) and 3-nitrobenzaldehyde (19 g, 125 mmol, 1.0 eq) in MeOH (500 mL) were added $NaBH(OAc)_3$ (53 g, 250 mmol, 2.0 eq) and acetic acid (1 mL). Then the resulting mixture was stirred at 30° C. overnight. LC-MS indicated complete conversion. The solvent was removed under vaccum and the residue was purified by column chromatography (DCM:MeOH=15:1), to provide tert-butyl N-{1-(3-nitrobenzyl)piperidin-4-yl}carbamate (32 g, 76%) as a white solid.

Tert-butyl N-{1-(3-nitrobenzyl)piperidin-4-yl}carbamate (30.0 g, 89.5 mmol, 1.0 eq)) was dissolved in 300 mL of TFA:DCM (1:10) and the resulting solution stirred at 30° C. overnight. The reaction mixture was then concentrated under vacuum to provide crude 1-(3-nitrobenzyl)piperidin-4-amine (33 g, TFA salt) as a white solid.

To a solution of 1-(3-nitrobenzyl)piperidin-4-amine (33 g, 69.6 mmol, 1.2 eq) in toluene (500 mL) were added 5-bromoisoquinoline (12 g, 58.0 mmol, 1.0 eq), BINAP (3.6 g, 5.8 mmol, 0.1 eq), NaOtBu (33 g, 347.8 mmol, 6.0 eq) and Pd$_2$(dba)$_3$ (5.3 g, 5.8 mmol, 0.1 eq). The reaction mixture was submitted to 3 vaccum-N$_2$ cycles and then stirred at 80° C. overnight. LC-MS indicated complete conversion. Toluene was removed under reduced pressure and the residue was purified by column chromatography (DCM:MeOH=15:1) to provide intermediate 6 (15 g, 71%) as a yellow solid.

Intermediates 7-13

The experimental protocol used for synthesis of intermediate 4 was used with minimal changes for synthesis of intermediates 7-13; which can be obtained by reacting intermediates 1-3 with the appropriate, commercially available reagents.

| Intermediate | IUPAC Name |
| --- | --- |
| 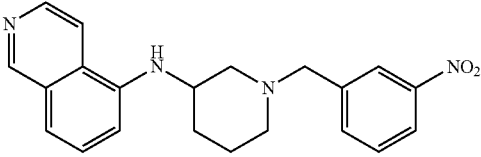<br>Intermediate 7 | N-(1-(3-nitrobenzyl)piperidin-3-yl)isoquinolin-5-amine |
| 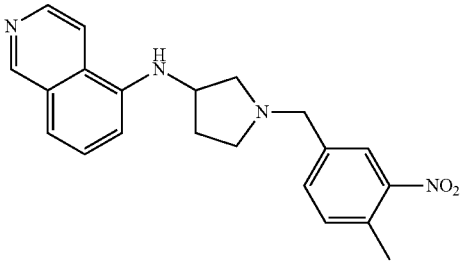<br>Intermediate 8 | N-(1-(3-nitro-4-methylbenzyl)pyrrolidin-3-yl)isoquinolin-5-amine |
| 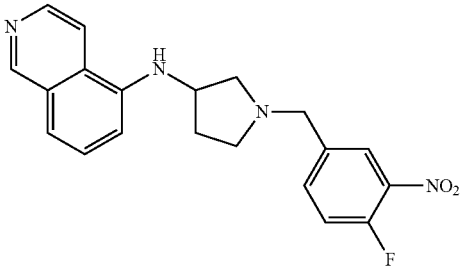<br>Intermediate 9 | N-(1-(3-nitro-4-fluorobenzyl)pyrrolidin-3-yl)isoquinolin-5-amine |
| 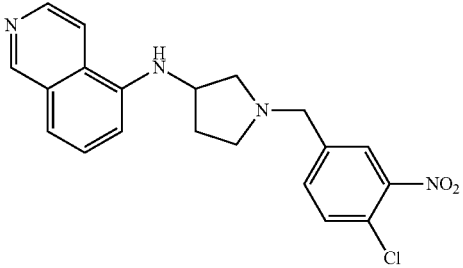<br>Intermediate 10 | N-(1-(3-nitro-4-chlorobenzyl)pyrrolidin-3-yl)isoquinolin-5-amine |

| Intermediate | IUPAC Name |
|---|---|
| 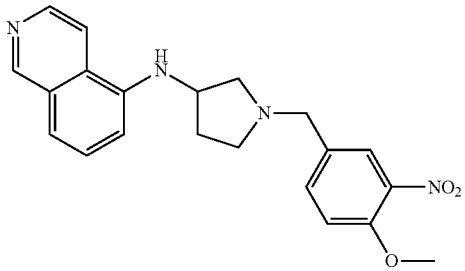<br>Intermediate 11 | N-(1-(3-nitro-4-methoxybenzyl)pyrrolidin-3-yl)isoquinolin-5-amine |
| 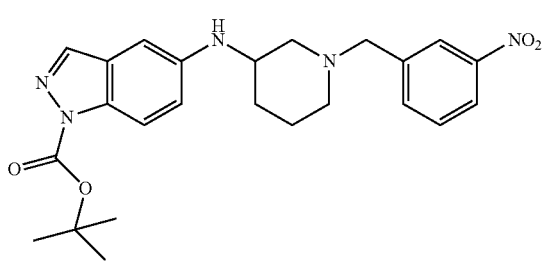<br>Intermediate 12 | 5-(N-(3-nitrobenzyl)piperidin-3-ylamino)-indazole-1-carboxylic acid tert-butyl ester |
| 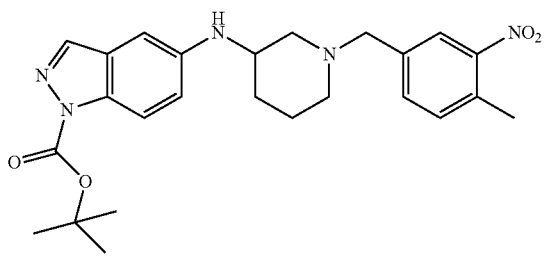<br>Intermediate 13 | 5-(N-(3-nitro-4-methylbenzyl)piperidin-3-ylamino)-indazole-1-carboxylic acid tert-butyl ester |

Intermediate 14: N-(1-(3-aminobenzyl)pyrrolidin-3-yl)isoquinolin-5-amine

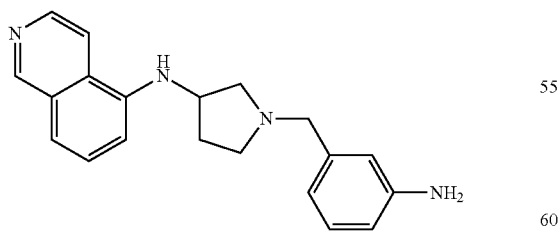

A mixture of intermediate 4 (5.2 g, 15 mmol) and Fe (4.2 g, 75 mmol) in EtOH (100 mL) was added sat.NH₄Cl (90 mL). The mixture was stirred at 80° C. overnight, filtered and concentrated under vacuum. The residue was purified by column chromatography to give the intermediate 14 (4 g, 88%).

Intermediate 15: 5-(N-(3-amino-4-methylbenzyl)piperidin-3-ylamino)-indazole-1-carboxylic acid tert-butyl ester

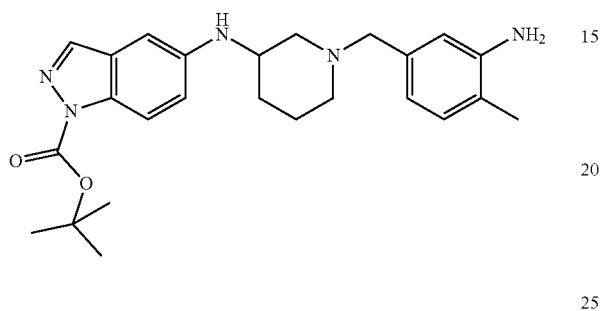

To a solution of intermediate 13 (1.68 g, 3.61 mmol, 1.0 eq) in MeOH (50 mL) was added Pd/C (0.192 g, 0.180 mmol, 0.05 eq) and ammonium formate (3.41 g, 54.1 mmol, 15.0 eq) portionwise. The mixture was stirred at 50° C. for 30 minutes, then filtered over celite, washed with MeOH and concentrated. The obtained green residue was dissolved in EtOAc and the resulting solution washed with sat.NaHCO$_3$, sat.NH$_4$Cl (5×) and brine, dried over Na$_2$SO$_4$, filtered, concentrated under vacuum to afford intermediate 15 (1.17 g, 69%) as a green crystal powder which was used directly in the next step without further purification.

Intermediate 16: 5-(N-(3-aminobenzyl)piperidin-3-ylamino)-indazole-1-carboxylic acid tert-butyl ester

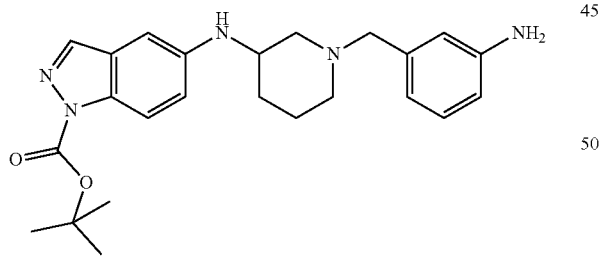

Intermediate 16 was obtained from intermediate 12 by following the procedure described for the intermediate 15.

Intermediates 17-23

The experimental protocol used for synthesis of intermediate 14 was used with minimal changes for reduction of the nitro group present in intermediates 5-13; thereby providing intermediates 17-23.

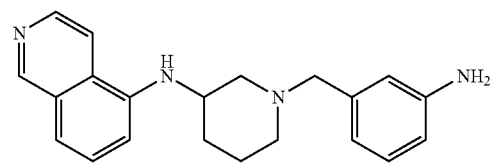

Intermediate 17: N-(1-(3-aminobenzyl)piperidin-3-yl)isoquinolin-5-amine

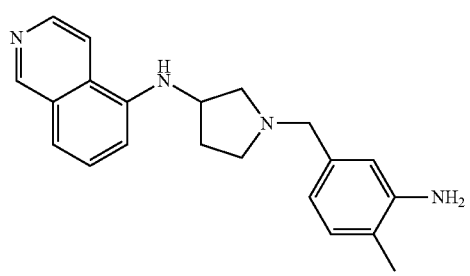

Intermediate 18: N-(1-(3-amino-4-methylbenzyl)pyrrolidin-3-yl)isoquinolin-5-amine

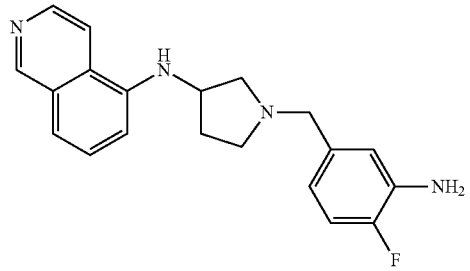

Intermediate 19: N-(1-(3-amino-4-fluorobenzyl)pyrrolidin-3-yl)isoquinolin-5-amine

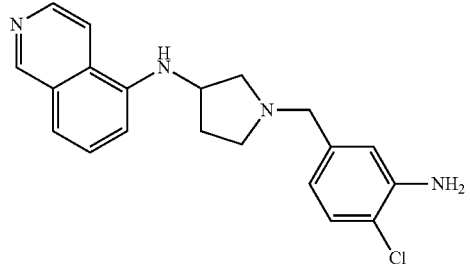

Intermediate 20: N-(1-(3-amino-4-chlorobenzyl)pyrrolidin-3-yl)isoquinolin-5-amine -continued

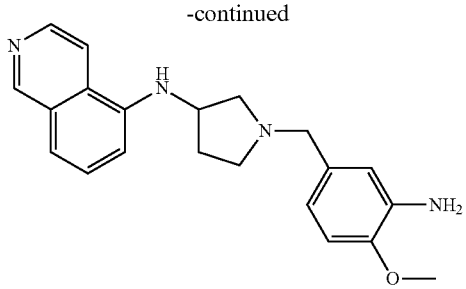

Intermediate 21: N-(1-(3-amino-4-methoxy benzyl)pyrrolidin-3-yl)isoquinolin-5-amine

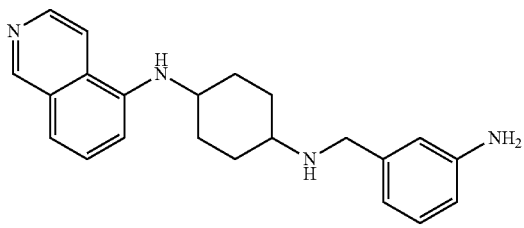 [SMILES: O=[N+]([O-])c1cccc(CNC2CCC(Nc3cccc4cnccc34)CC2)c1]

Intermediate 22: 1-N-(isoquinolin-5-yl)-4-N-(3-aminobenzyl)cyclohexane-1,4-diamine

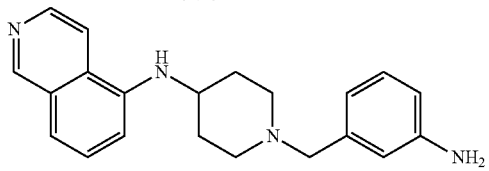 [SMILES: O=[N+]([O-])c1cccc(CN2CCC(Nc3cccc4cnccc34)CC2)c1]

Intermediate 23: N-{1-(3-aminobenzyl)piperidin-4-yl}isoquinolin-5-amine.

B.2. Compounds of the Invention

B.2.1. Methyl Esters

Compound 1: Methyl 3-((3-((3-(isoquinolin-5-ylamino)pyrrolidin-1-yl)methyl)phenyl)carbamoyl)benzoate

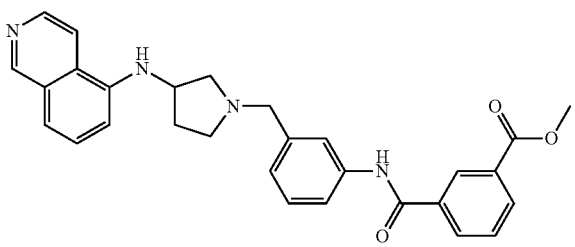 [SMILES: COC(=O)c1cccc(C(=O)Nc2cccc(CN3CCC(Nc4cccc5cnccc45)C3)c2)c1]

To a suspension of intermediate 14 (1 g, 3.14 mmol) and 3-(methoxycarbonyl)benzoic acid (0.594 g, 3.30 mmol, 1.05 eq) in DCM (15 mL) was added at 0° C. the 2,4,6-tripropyl-1,3,5,2,4,6-trioxatriphosphinane 2,4,6-trioxide (5.61 ml, 9.42 mmol, 3 eq) and the N,N-dimethylpyridin-4-amine (1.535 g, 12.56 mmol, 4 eq). The reaction mixture was stirred at rt for 2 h, diluted in EtOAc, washed with sat.NaHCO₃ and brine, dried over Na₂SO₄ and concentrated under vacuum. The residue was purified by reverse phase flash chromatography eluting with Water/ACN 100/0 to 0/100 to give the title compound (1 g, 66%) as a white powder.

Compound 2: Methyl 4-((3-((3-(isoquinolin-5-ylamino)pyrrolidin-1-yl)methyl)phenyl)carbamoyl)benzoate

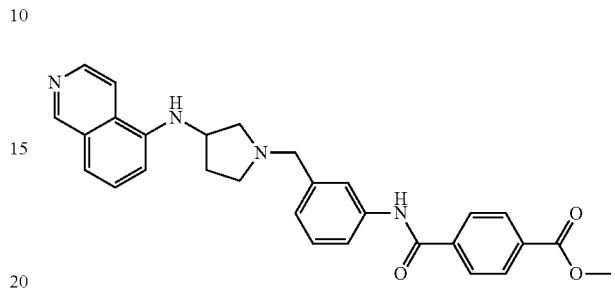

To a suspension of intermediate 14 (1.5 g, 4.71 mmol) and 4-(methoxycarbonyl)benzoic acid (0.891 g, 4.95 mmol, 1.05 eq) in DCM (22 mL) was added at 0° C. the 2,4,6-tripropyl-1,3,5,2,4,6-trioxatriphosphinane 2,4,6-trioxide (50% in EtOAc, 8.41 ml, 14.13 mmol, 3 eq) and the N,N-dimethylpyridin-4-amine (2.302 g, 18.84 mmol, 4 eq). The reaction mixture was stirred at rt for 2 h, diluted in EtOAc, washed with saturated NaHCO₃ and brine, dried over Na₂SO₄ and concentrated under vacuum. The residue was purified by reverse phase flash chromatography eluting with Water/ACN 100/0 to 0/100 to give the title compound (1.54 g, 68%) as a white powder.

Compound 3: Methyl 3-((5-((3-((1H-indazol-5-yl)amino)piperidin-1-yl)methyl)-2-methylphenyl)carbamoyl)benzoate dihydrochloride

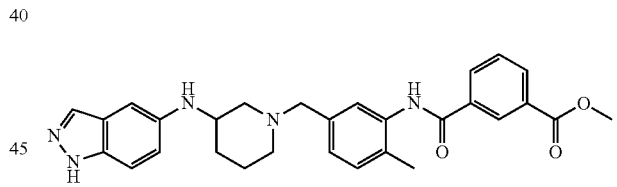

To a solution of intermediate 15 (100 mg, 0.230 mmol, 1.0 eq) and 3-(methoxycarbonyl)benzoic acid (41 mg, 0.230 mmol, 1.0 eq) in DCM (1.5 mL) was added at 0° C. 2,4,6-tripropyl-1,3,5,2,4,6-trioxatriphosphinane 2,4,6-trioxide (0.410 mL, 0.689 mmol, 3.0 eq). After 5 minutes of stirring at 0° C., DMAP (112 mg, 0.918 mmol, 4.0 eq) was added and the solution stirred at 0° C. for 1 hour, then slowly allowed to warm to room temperature and stirred overnight. The solution was diluted with EtOAc, washed with sat. NaHCO₃, sat. NH₄Cl (×2) and brine, then dried over Na₂SO₄, filtered and concentrated under vacuum. The residue was dissolved in DCM and purified by flash chromatography eluting with (DCM:MeOH=98:2) to give the Boc-compound 3.

To a solution of Boc-compound 3 in DCM (5 mL) was bubbled HCl gas for 5 min. The resulting mixture was stirred for 1 hour and concentrated under vacuum. The residue was purified by reversed phase flash chromatography eluting with ACN/H₂O(0.1% TFA), 0/100 to 30/70 to give the compound 3 (76 mg, 58%) as a beige powder.

The following compounds of the invention can be synthesized by reacting the appropriate intermediates with commercially available reagents, by following procedures analogous to those used for obtaining compounds 1-3.

| Compound | Structure |
|---|---|
| 4 | 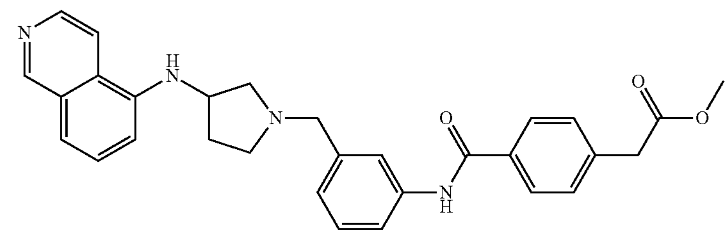 [SMILES: COC(=O)Cc1ccc(C(=O)Nc2cccc(CN3CCC(Nc4cccc5cnccc45)C3)c2)cc1] |
| 5 | 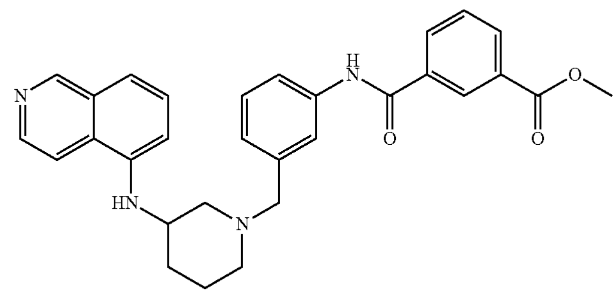 [SMILES: COC(=O)c1cccc(C(=O)Nc2cccc(CN3CCCC(Nc4cccc5cnccc45)C3)c2)c1] |
| 6 | 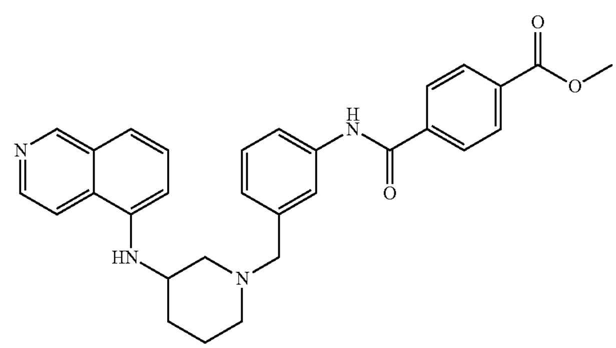 [SMILES: COC(=O)c1ccc(C(=O)Nc2cccc(CN3CCCC(Nc4cccc5cnccc45)C3)c2)cc1] |
| 7 | 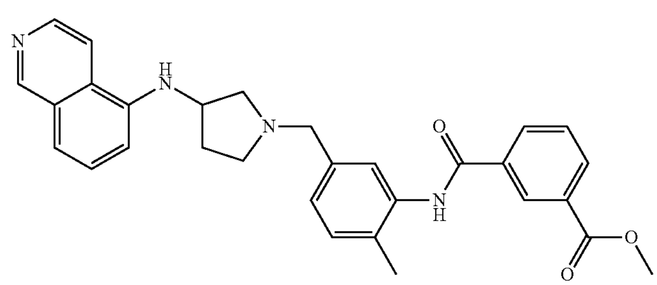 [SMILES: COC(=O)c1cccc(C(=O)Nc2cc(CN3CCC(Nc4cccc5cnccc45)C3)ccc2C)c1] |
| 8 | 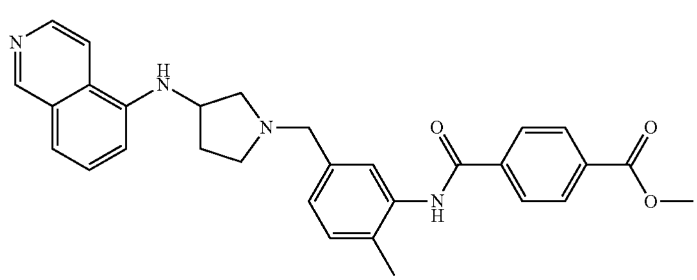 [SMILES: COC(=O)c1ccc(C(=O)Nc2cc(CN3CCC(Nc4cccc5cnccc45)C3)ccc2C)cc1] |

-continued
| Compound | Structure |
|---|---|
| 9 | 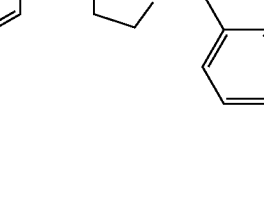 |
| 10 | 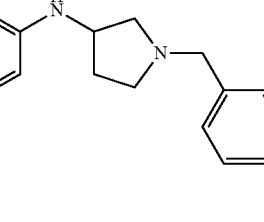 |
| 11 | 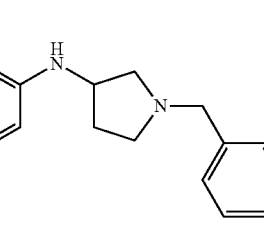 |
| 12 | 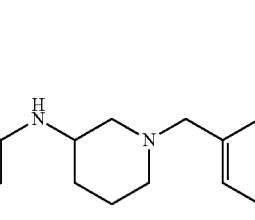 |
| 13 | 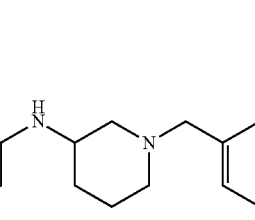 |
| 14 | 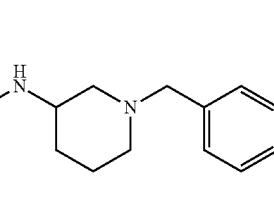 |

-continued

| Compound | Structure |
|---|---|
| 15 | 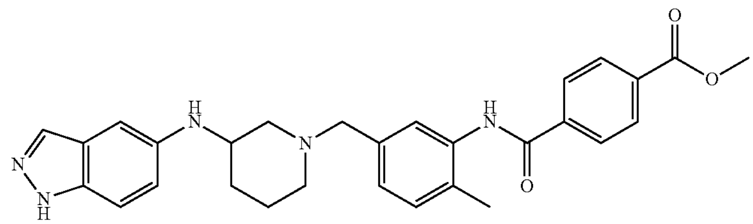 [SMILES: COC(=O)c1ccc(C(=O)Nc2cc(CN3CCCC(Nc4ccc5[nH]ncc5c4)C3)ccc2C)cc1] |
| 16 | 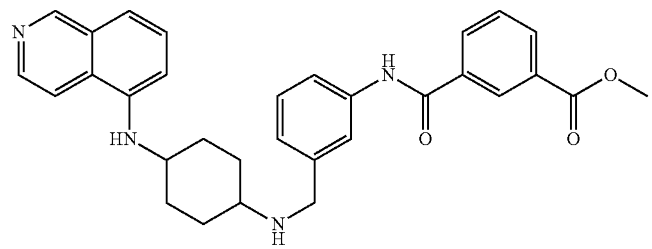 [SMILES: COC(=O)c1cccc(C(=O)Nc2cccc(CNC3CCC(Nc4cccc5cnccc45)CC3)c2)c1] |
| 17 | 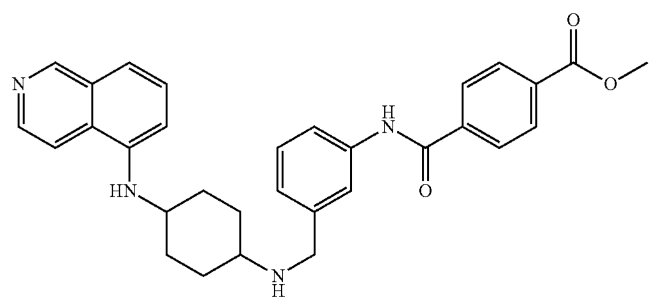 [SMILES: COC(=O)c1ccc(C(=O)Nc2cccc(CNC3CCC(Nc4cccc5cnccc45)CC3)c2)cc1] |
| 18 | 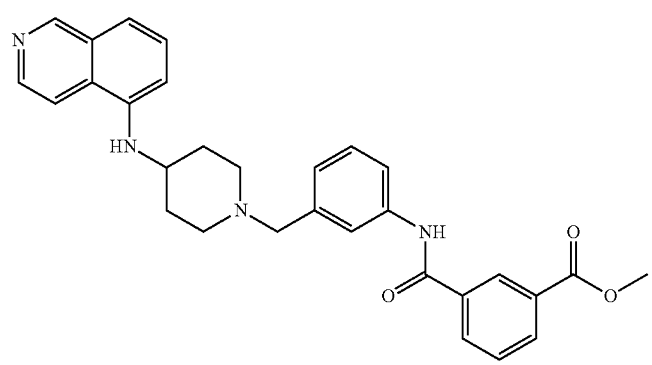 [SMILES: COC(=O)c1cccc(C(=O)Nc2cccc(CN3CCC(Nc4cccc5cnccc45)CC3)c2)c1] |

|Compound|Structure|
|---|---|
|19|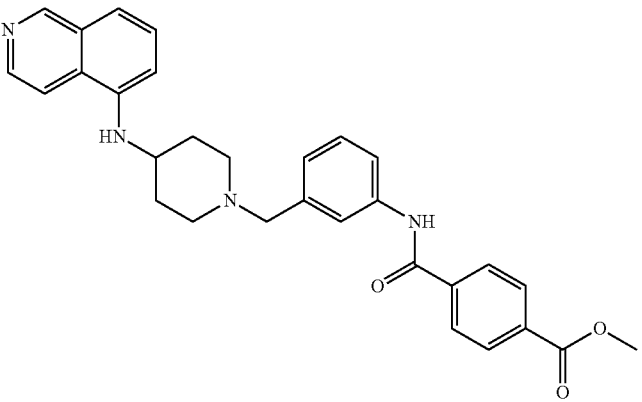 [SMILES: COC(=O)c1ccc(C(=O)Nc2cccc(CN3CCC(Nc4cccc5cnccc45)CC3)c2)cc1]|

| Compound | Structure |
|---|---|
| 20 | 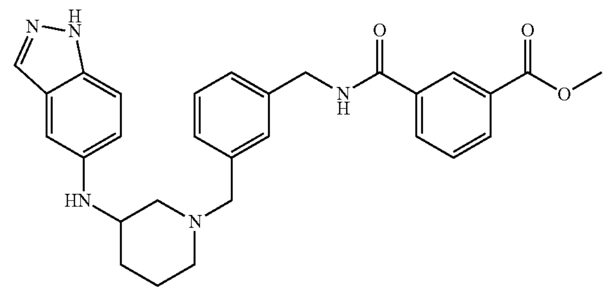 [SMILES: COC(=O)c1cccc(C(=O)NCc2cccc(CN3CCCC(Nc4ccc5[nH]ncc5c4)C3)c2)c1] |

-continued

B.2.2. Additional Esters

B.2.2.1: Carboxylic Acid Intermediates

Intermediate 24: 3-((3-((3-(isoquinolin-5-ylamino)pyrrolidin-1-yl)methyl)phenyl)carbamoyl)benzoic acid

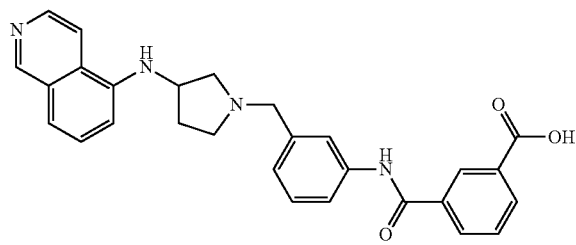 [SMILES: O=C(O)c1cccc(C(=O)Nc2cccc(CN3CCC(Nc4cccc5cnccc45)C3)c2)c1]

To a solution of Compound 1 (1 g, 2.081 mmol) in THF (12 mL) was added a solution of LiOH (0.150 g, 6.24 mmol, 3 eq) in Water (6.00 mL). Then the reaction mixture was stirred at rt for 2 h and the THF removed by distillation under vacuum. The resulting aqueous layer was acidified by addition of sat $NH_4Cl$ and the precipitate collected by filtration and washed with water to give intermediate 24 (835 mg, 86%) as a yellow powder.

Intermediate 25: 4-((3-((3-(isoquinolin-5-ylamino)pyrrolidin-1-yl)methyl)phenyl)carbamoyl)benzoic acid

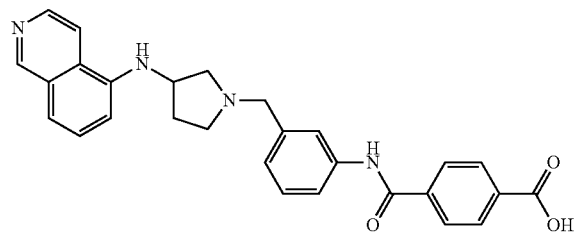 [SMILES: O=C(O)c1ccc(C(=O)Nc2cccc(CN3CCC(Nc4cccc5cnccc45)C3)c2)cc1]

To a solution of Compound 2 (1.54 g, 3.20 mmol) in THF (18 mL) was added a solution of LiOH (0.230 g, 9.61 mmol, 3 eq) in Water (9.00 mL). Then the reaction mixture was stirred at rt for 2 h and the THF removed by distillation under vacuum. The resulting aqueous layer was acidified by addition of sat $NH_4Cl$ and the precipitate collected by filtration and washed with water to give the intermediate 25 (1.1 g, 74%) as a yellow powder.

Additional carboxylic intermediates can be synthesized via saponification of the methyl ester present in compounds 1-20 following similar procedures. For indazole derivatives, it is advisable to perform the saponification reaction prior to deprotection of the indazole. Alternatively, the indazole structure present in compounds of the invention such as compounds 3, 12, 13, 14, 15 or 20 can be protected again before saponification; the corresponding procedures being obvious to those skilled in the art.

B 2.2.2. General Procedures for Ester Formation

Protocol A (isoquinoline derivatives): To a suspension of carboxylic acid intermediate (100 mg, 1.0 eq) and R—OH (10 eq) in DCM (1 mL) was added at 0° C. the 2,4,6-tripropyl-1,3,5,2,4,6-trioxatriphosphinane 2,4,6-trioxide (50% in EtOAc, 3 eq) and the N,N-dimethylpyridin-4-amine (4 eq). The reaction mixture was stirred at rt for 2 h, diluted in EtOAc, washed with saturated $NaHCO_3$ and brine, dried over $Na_2SO_4$ and concentrated under vacuum. The residue was purified by reverse phase flash chromatography eluting with Water/ACN 100/0 to 0/100 to give the expected compound.

Protocol B (indazole derivatives): To a suspension of carboxylic acid intermediate (100 mg, 1.0 eq) and R—OH (10 eq) in DCM (1 mL) was added at 0° C. the 2,4,6-tripropyl-1,3,5,2,4,6-trioxatriphosphinane 2,4,6-trioxide (50% in EtOAc, 3 eq) and the N,N-dimethylpyridin-4-amine (4 eq). The reaction mixture was stirred at rt for 2 h, diluted in EtOAc, washed with saturated $NaHCO_3$ and brine, dried over $Na_2SO_4$ and concentrated under vacuum. The residue was dissolved in 4 mL of a solution of TFA in DCM (1:4) and the reaction mixture was stirred at 30° C. for 4 h. Then the solvent was evaporated and the residue purified by reverse phase flash chromatography eluting with Water/ACN 100/0 to 0/100 to give the expected compound.

B 2.2.3. Additional Compounds of the Invention

The following compounds of the invention were synthesized by following the general procedures described above (B 2.2.1 and B 2.2.2).

| Compound | Structure |
|---|---|
| 21 | 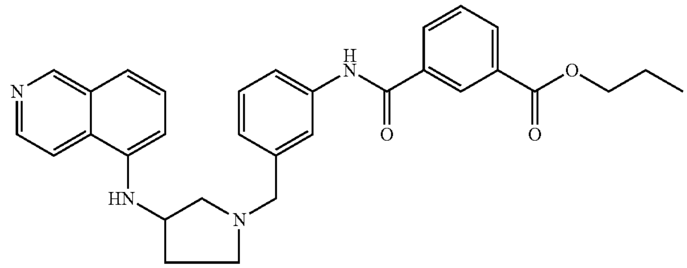 [SMILES: CCCOC(=O)c1cccc(C(=O)Nc2cccc(CN3CCC(Nc4cccc5cnccc45)C3)c2)c1] |
| 22 | 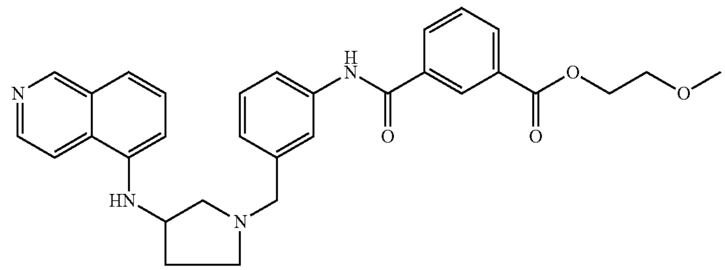 [SMILES: COCCOC(=O)c1cccc(C(=O)Nc2cccc(CN3CCC(Nc4cccc5cnccc45)C3)c2)c1] |
| 23 | 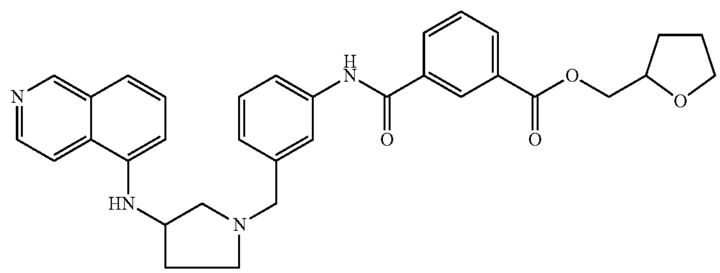 [SMILES: O=C(Nc1cccc(CN2CCC(Nc3cccc4cnccc34)C2)c1)c1cccc(C(=O)OCC2CCCO2)c1] |
| 24 | 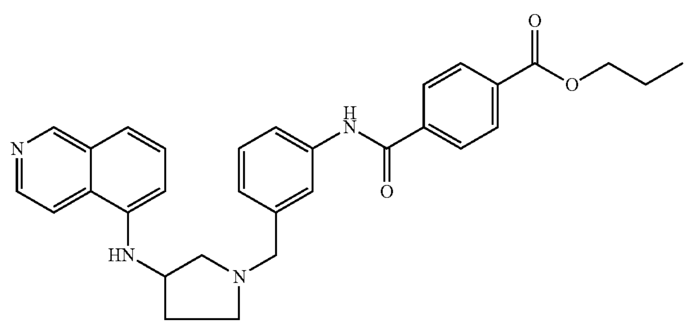 [SMILES: CCCOC(=O)c1ccc(C(=O)Nc2cccc(CN3CCC(Nc4cccc5cnccc45)C3)c2)cc1] |
| 25 | 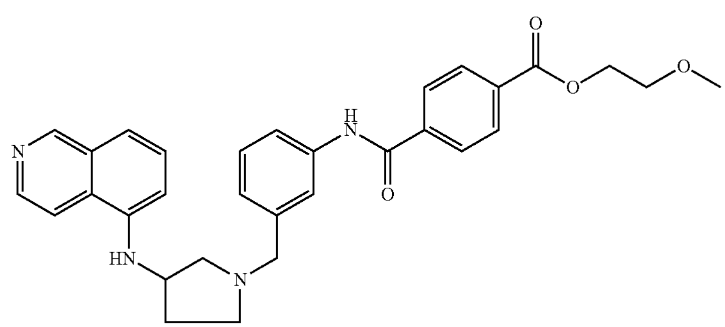 [SMILES: COCCOC(=O)c1ccc(C(=O)Nc2cccc(CN3CCC(Nc4cccc5cnccc45)C3)c2)cc1] |

-continued

| Compound | Structure |
|---|---|
| 26 | (isoquinolin-5-yl)amino-pyrrolidin-1-ylmethyl-phenyl-NHC(O)-C6H4-C(O)O-CH2-(tetrahydrofuran-2-yl) |
| 27 | (isoquinolin-5-yl)amino-cyclohexyl-NH-CH2-phenyl-NHC(O)-C6H4-C(O)O-propyl (meta ester) |
| 28 | (isoquinolin-5-yl)amino-cyclohexyl-NH-CH2-phenyl-NHC(O)-C6H4-C(O)O-CH2CH2-OCH3 (meta ester) |
| 29 | (isoquinolin-5-yl)amino-cyclohexyl-NH-CH2-phenyl-NHC(O)-C6H4-C(O)O-CH2-(tetrahydrofuran-2-yl) (meta ester) |
| 30 | (isoquinolin-5-yl)amino-cyclohexyl-NH-CH2-phenyl-NHC(O)-C6H4-C(O)O-propyl (para ester) |

-continued
| Compound | Structure |
|---|---|
| 31 | 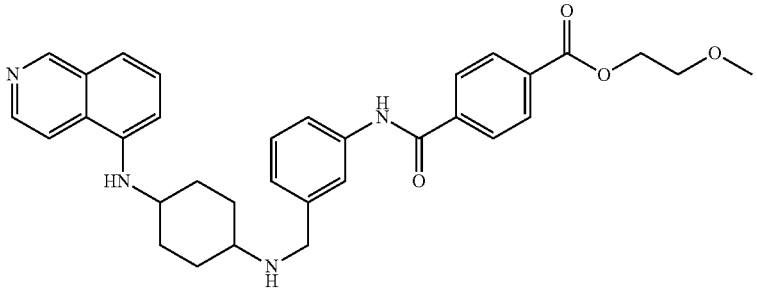 [SMILES: COCCOC(=O)c1ccc(C(=O)Nc2cccc(CNC3CCC(Nc4cccc5cnccc45)CC3)c2)cc1] |
| 32 | 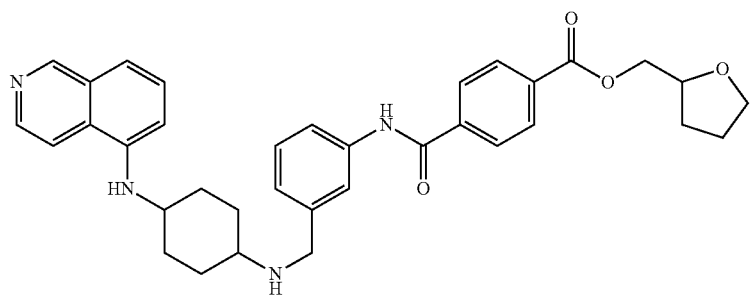 [SMILES: O=C(Nc1cccc(CNC2CCC(Nc3cccc4cnccc34)CC2)c1)c1ccc(C(=O)OCC2CCCO2)cc1] |
| 33 | 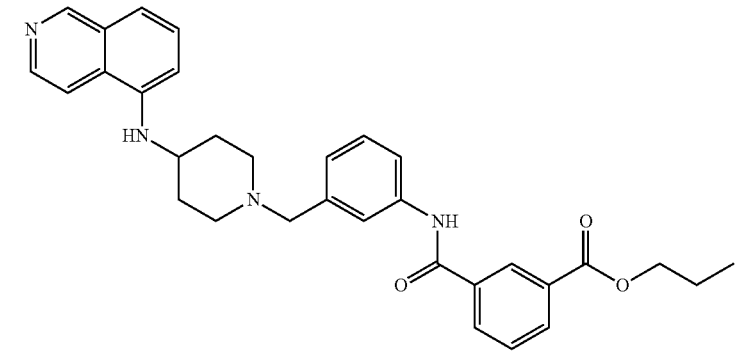 [SMILES: CCCOC(=O)c1cccc(C(=O)Nc2cccc(CN3CCC(Nc4cccc5cnccc45)CC3)c2)c1] |
| 34 | 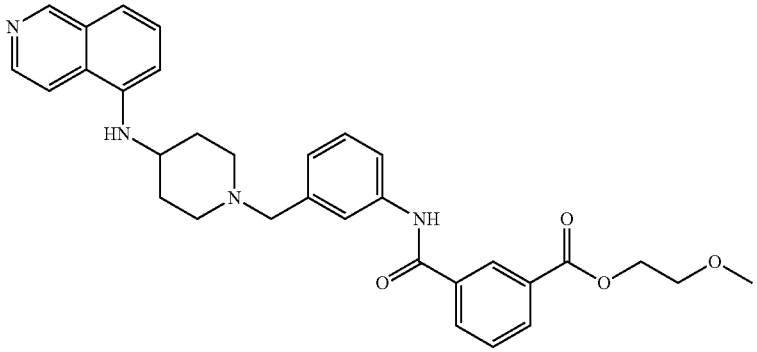 [SMILES: COCCOC(=O)c1cccc(C(=O)Nc2cccc(CN3CCC(Nc4cccc5cnccc45)CC3)c2)c1] |

| Compound | Structure |
|---|---|
| 35 | 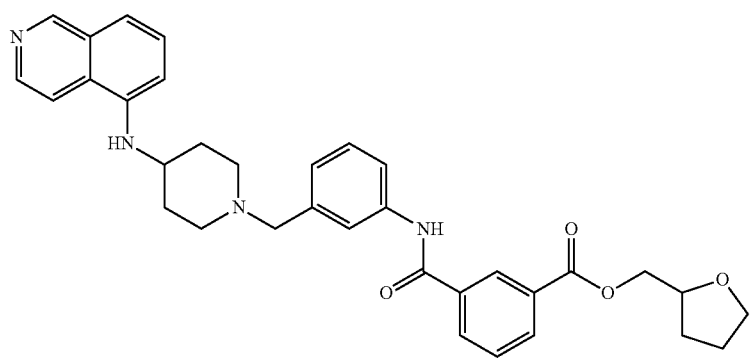 [SMILES: O=C(Nc1cccc(CN2CCC(Nc3cccc4cnccc34)CC2)c1)c1cccc(C(=O)OCC2CCCO2)c1] |
| 36 | 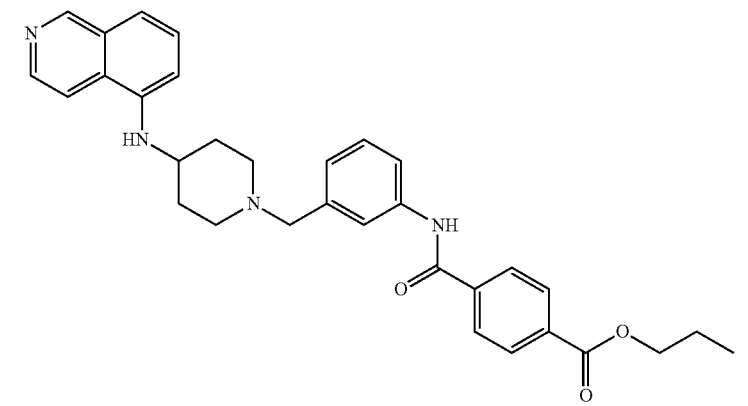 [SMILES: CCCOC(=O)c1ccc(C(=O)Nc2cccc(CN3CCC(Nc4cccc5cnccc45)CC3)c2)cc1] |
| 37 | 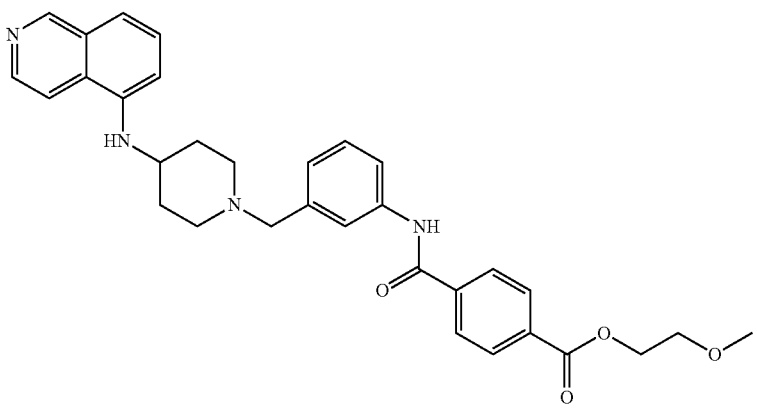 [SMILES: COCCOC(=O)c1ccc(C(=O)Nc2cccc(CN3CCC(Nc4cccc5cnccc45)CC3)c2)cc1] |
| 38 | 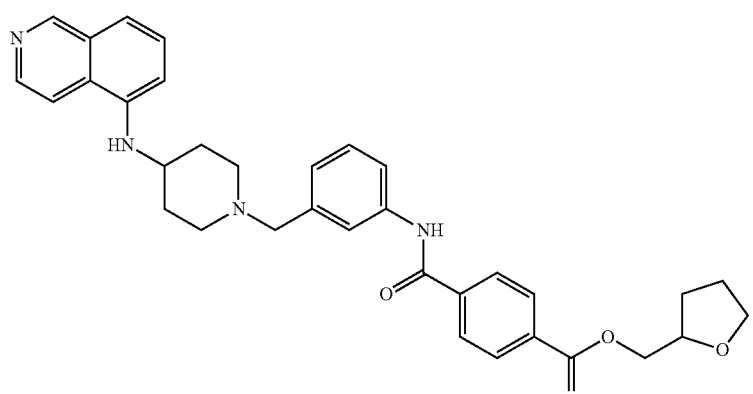 |

-continued
| Compound | Structure |
|---|---|
| 39 | 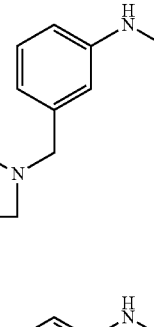 |
| 40 | 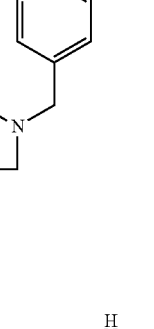 |
| 41 | 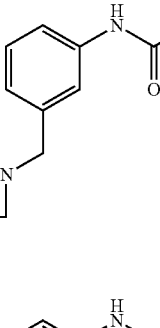 |
| 42 | 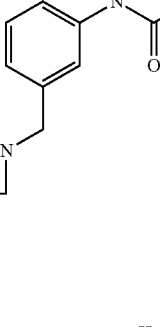 |
| 43 | 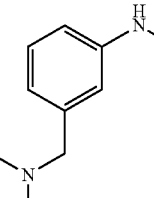 |

| Compound | Structure |
|---|---|
| 44 | (structure: isoquinoline-NH-pyrrolidine-CH2-N linked benzyl-NH-C(=O)-benzene-C(=O)-O-oxetane) |

C. In Vitro and In Vivo Assays

C.1. ROCK Inhibitory Activity Screening

C.1.1. Kinase Inhibition (ROCKI & ROCKII)

On-target activity against ROCK was measured in a biochemical assay, using the following reagents: Base Reaction buffer; 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO. Required cofactors are added individually to each kinase reaction. The reaction procedure first involved the preparation of a peptide substrate in a freshly prepared reaction buffer. Required cofactors were then added to the substrate solution. ROCK (1 nM final concentration) was then delivered to the substrate solution. After gentle mix, DMSO solutions of the test compounds were added to the enzyme. Substrate mix $^{33}$P-ATP (specific activity 0.01 µCi/µl final) was then delivered into the reaction mixture to initiate the reaction. The kinase reaction was incubated for 120 min. at room temperature. Reactions were then spotted onto P81 ion exchange paper (Whatman #3698-915). Filters were washed extensively in 0.1% Phosphoric acid. A radiometric count was then performed and $IC_{50}$ values were subsequently determined.

The $IC_{50}$ values obtained (in accordance with the protocol set forth above) are represented as follows: "+++" means $IC_{50}$ below 0.1 µM, "++" means $IC_{50}$ between 0.1 µM and 1 µM; "+" means $IC_{50}$ between 1 and 10 µM and "ND" means "not determined yet".

| # Cpds | $IC_{50}$ ROCK2 |
|---|---|
| 1 | +++ |
| 2 | +++ |
| 16 | +++ |
| 17 | +++ |
| 18 | +++ |
| 19 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | +++ |

C.1.2. Myosin Light Chain Phosphorylation Assay

Rat smooth muscle cell line A7r5 is used. The endogenous expression of ROCK results in a constitutive phosphorylation of the regulatory myosin light chain at T18/S19. A7r5 cells were plated in DMEM supplemented with 10% FCS in multiwall cell culture plates. After serum starvation overnight, cells were incubated with compounds in serum-free medium.

Quantification of MLC-T18/S19 phosphorylation is assesses in 96 well-plates via ELISA using a phspho-MLC-T18/S19 specific antibody and a secondary detection antibody. Relative MLC phosphorylation is measured with respect to untreated cells (Positive control, 1.0) and cells treated with 100 µM Y-27632 (Negative control, 0.0). $EC_{50}$ values were determined using GraphPad Prism 5.01 software using a nonlinear regression curve fit with variable hill slope.

The $EC_K$ values obtained (in accordance with the protocols set forth above) are represented as follows: "+++" means $EC_{50}$ below 0.3 µM, "++" means $EC_{50}$ between 0.3 µM and 1 µM; "+" means $EC_{50}$ between 1 and 10 µM and "–" means $EC_{50}$>10 µM.

| # Cpds | $EC_{50}$ |
|---|---|
| 1 | +++ |
| 2 | +++ |
| 16 | +++ |
| 21 | +++ |
| 22 | +++ |
| 24 | +++ |
| 32 | ++ |
| 34 | ++ |
| Y-27632 | ++ |
| Fasudil | + |

In addition to this data, FIG. 1 provides the concentration-response curves for compound 32 and Met1, the predicted metabolite of compound 14 resulting from ester hydrolysis by carboxylic ester hydrolases. As will be demonstrated in point C2, such hydrolysis readily occurs in plasma. FIG. 1 further exemplifies the difference of activity (>20-fold difference in $EC_{50}$ values) between compound 32 which represents a functionally active compound and its metabolite Met1 and thereby further demonstrates the soft character of compound 32.

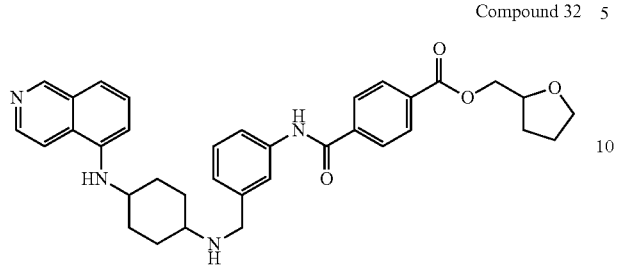

Compound 32

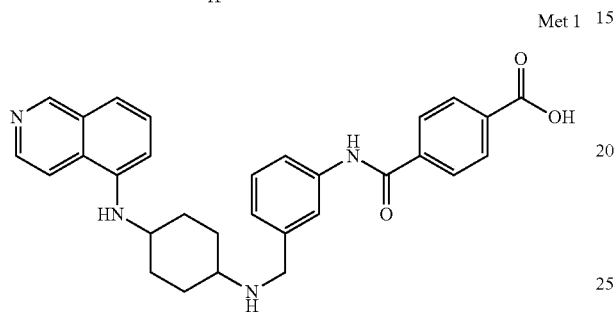

Met 1

C.2. Pharmacological Characterization

C.2.1. Stability Assay in Human (Animal) Plasma/Whole Blood

Compounds are incubated at a concentration of 1 µM in human or animal (rat, mice or rabbit) human plasma or whole blood. Samples are taken at fixed time points and the remnant of compound is determined by LC-MS/MS after protein precipitation. Half life is expressed in minutes.

| # Cpd | t½ human plasma | t½ human whole blood |
|---|---|---|
| 3 | 33 | NT |
| 7 | 31 | NT |
| 16 | <20 | NT |
| 21 | <20 | <20 |
| 22 | <20 | <20 |
| 23 | <20 | <20 |
| 27 | <20 | NT |
| 28 | <20 | NT |
| 29 | <20 | NT |
| 32 | 20 | NT |
| 33 | <20 | NT |
| 34 | <20 | NT |
| 35 | <20 | NT |

C.2.2. Stability Assay in Rabbit Aqueous Humor

Compounds are incubated at a concentration of 1 µM in rabbit aqueous humor (AH). Samples are taken at fixed time points and the remnant of compound is determined by LC-MS/MS after protein precipitation. Half life is expressed in minutes.

| # Cpd | t½ AH |
|---|---|
| 1 | >120 |
| 3 | >120 |
| 7 | >120 |
| 15 | >120 |
| 21 | 120 |
| 22 | >120 |
| 23 | 77 |
| 27 | >120 |
| 28 | >120 |
| 29 | >120 |
| 33 | >120 |
| 34 | >120 |
| 35 | >120 |

C3. Comparison to Structurally Related Compounds

Compared to structurally similar prior art known ROCK inhibitors, such as for example described in WO2008/077057, WO2010/065782, WO2009/158587, US2009/0325960, US2009/0325959, Iwakubo et al. (*Bioorg. Med. Chem.*, 2007, 15, 350-364 & Bioorg. Med. Chem., 2007, 15, 1022-1033) and WO2001/56988, the compounds of the present invention differ in that they are very rapidly converted into predictable, functionally inactive compounds when entering systemic circulation, yet retain good stability in target organs. While the above-mentioned documents disclose ROCK inhibitors that are structurally similar to the compounds of this invention, none of these documents discusses the design, discovery or potential advantages of soft ROCK inhibitors. In particular, no information is provided regarding the stability of the disclosed ROCK inhibitors in plasma, whole blood, or in potential target organs.

Document WO2012/015760 discloses ester-containing isoquinoline and indazole derivatives that are prodrug forms of Rho-kinase inhibitors, as evidenced by the document abstract, stating explicitly that "These prodrugs are in general the ester or the amide derivatives of the parent compounds. These prodrugs are often weak inhibitors of ROCK, but their parent compounds have good activities. Upon instillation into the eyes, the ester or the amide group of these prodrugs is rapidly hydrolyzed into alcohol, amine or acid, and the prodrugs are converted into the active base compounds. The prodrugs of the ROCK inhibitors provide several advantages such as delivery of higher concentrations of the active species into the target site". The pharmacological profile of compounds disclosed in WO2012/015760 (Prodrug; weakly active compound with low stability in target organ; yielding a functionally active compound upon hydrolysis) is by definition surprisingly opposite to the pharmacological profile displayed by compounds of the invention (Soft drug, highly active compound with good stability in target organ but poor stability in systemic circulation; yielding a functionally inactive compound upon hydrolysis).

Additionally, it will be noted that the ester-containing indazole or isoquinoline derivatives cited in WO2008/077057, WO2010/065782, WO2009/158587, US2009/0325960, or US2009/0325959 and displaying good inhibitory potency against ROCK1 and/or ROCK2 (namely 1.060, 1.147, 1.187, 1.200, 1.224, 1.225, 2.071) are later described as WO2012/015760 and are therefore expected to display a prodrug profile, instead of a soft drug profile.

The invention claimed is:
1. A compound of Formula I or a stereoisomer, tautomer, racemic, salt, hydrate, or solvate thereof,

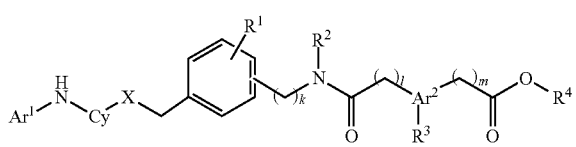

Wherein
Ar¹ is selected from

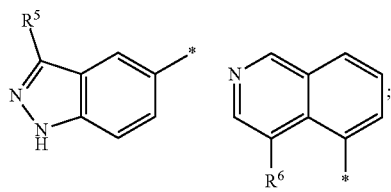

Ar² represents an aryl or heteroaryl;
Cy is a $C_{3-15}$cycloalkyl wherein optionally one carbon atom is replaced by a nitrogen atom;
X is a direct bond, —NH— or —N($C_{1-6}$alkyl)-;
R¹ is selected from hydrogen, halogen, $C_{1-6}$ alkyl, and $C_{1-6}$ alkoxyl;
R² is selected from hydrogen and $C_{1-3}$ alkyl;
R³ is selected from hydrogen, halogen, $C_{1-6}$ alkyl, and $C_{1-6}$ alkoxyl;
R⁴ is an optionally substituted group selected from $C_{1-20}$alkyl, $C_{2-20}$alkenyl, $C_{2-20}$alkynyl, $C_{3-15}$cycloalkyl, aryl, heterocyclyl, and heteroaryl;
R⁵ is selected from hydrogen, $C_{1-6}$alkyl and $NH_2$;
R⁶ is selected from hydrogen, halo or $C_{1-6}$alkyl;
k is an integer from 0 to 3;
l is an integer from 0 to 3;
m is an integer from 0 to 3.

2. The compound of claim 1, wherein
Ar¹ is selected from

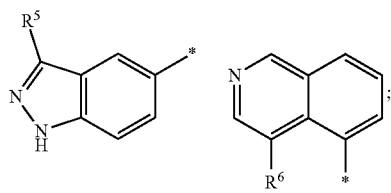

Ar² represents an aryl or heteroaryl;
Cy is a $C_{3-15}$cycloalkyl wherein optionally one carbon atom is replaced by a nitrogen atom;
X is a direct bond, —NH— or —N($C_{1-6}$alkyl)-;
R¹ is selected from hydrogen, halogen, $C_{1-6}$ alkyl, and $C_{1-6}$ alkoxyl;
R² is selected from hydrogen and $C_{1-3}$ alkyl;
R³ is selected from hydrogen, halogen, $C_{1-6}$ alkyl, and $C_{1-6}$ alkoxyl;
R⁴ is an optionally substituted group selected from $C_{1-20}$alkyl, $C_{2-20}$alkenyl, $C_{2-20}$alkynyl, $C_{3-15}$cycloalkyl, aryl, heterocyclyl, and heteroaryl;
R⁵ is selected from hydrogen, $C_{1-6}$alkyl and $NH_2$;
R⁶ is selected from hydrogen, halo or $C_{1-6}$alkyl;
k is an integer from 0 to 3;
l is an integer from 0 to 3;
m is an integer from 0 to 3;
with the proviso that when Cy contains a nitrogen atom, then X is a direct bond; and when Cy does not contain a nitrogen atom, then X is —N($C_{1-6}$alkyl)- or —NH—.

3. The compound of claim 1, wherein -Cy-X— is selected from the group consisting of:

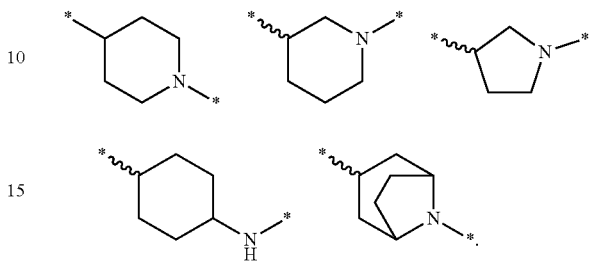

4. The compound of claim 1, wherein Ar² is aryl.

5. The compound of claim 1, wherein R¹ is selected from the group consisting of hydrogen, halogen, methyl, and methoxyl.

6. The compound of claim 1, wherein:
R² is hydrogen; and
R³ is hydrogen or $C_{1-6}$alkoxyl.

7. The compound of 1, wherein R⁴ is an optionally substituted group selected from the group consisting of $C_{1-20}$alkyl, $C_{3-15}$cycloalkyl, and heterocyclyl and wherein the optional substituents are selected from halo, hydroxyl, nitro, amino, cyano, aryl, cycloalkyl, heterocyclyl, and alkoxy.

8. The compound of claim 1, wherein
R⁵ is selected from the group consisting of hydrogen, methyl, and $NH_2$, or
R⁶ is hydrogen, fluoro, or methyl.

9. The compound of claim 1, wherein k, l, and m are each independently selected from 0 and 1.

10. A pharmaceutical composition comprising the compound as defined in claim 1, for use as a human or veterinary medicine.

11. A pharmaceutical composition comprising the compound as defined in 1 and one or more pharmaceutically acceptable carriers, diluents, excipients, or adjuvants.

12. A method for the treatment of at least one disease or disorder selected from eye diseases; lung diseases; and intestinal diseases; said method comprising administering to a subject in need thereof a therapeutic effective amount of the compound of claim 1.

13. The method of claim 12, wherein the at least one disease or disorder is an eye disease selected from the group consisting of retinopathy, optic neuropathy, glaucoma, inflammatory eye diseases and degenerative retinal diseases.

14. The method of claim 12, wherein the at least one disease or disorder is a lung disease selected from the group consisting of pulmonary fibrosis, emphysema, chronic bronchitis, asthma, fibrosis, pneumonia, cystic fibrosis, chronic obstructive pulmonary disease (COPD), bronchitis and rhinitis and respiratory distress syndrome.

15. The method of claim 12, wherein the at least one disease or disorder is an intestinal disease selected from the group consisting of inflammatory bowel disease (IBD), colitis, gastroenteritis, ileus, ileitis, appendicitis and Crohn's disease.

16. A method for inhibiting a rho-kinase in a subject, the method comprising administering a therapeutic effective amount of the compound of claim 1 to a subject in need thereof.

* * * * *